(12) United States Patent
Parazynski et al.

(10) Patent No.: US 11,253,670 B1
(45) Date of Patent: Feb. 22, 2022

(54) RESPIRATORY ISOLATION AND/OR TREATMENT DEVICES AND METHODS OF USING THE SAME

(71) Applicant: Apogee Innovations, Houston, TX (US)

(72) Inventors: Scott Edward Parazynski, Houston, TX (US); Jeffrey William Bull, Naperville, IL (US); Roy Melling, Borrego Springs, CA (US); Daniel Tagtow, Austin, TX (US)

(73) Assignee: Apogee Innovations, Houston, TX (US)

( * ) Notice: Subject to any disclaimer, the term of this patent is extended or adjusted under 35 U.S.C. 154(b) by 0 days.

(21) Appl. No.: 17/116,468

(22) Filed: Dec. 9, 2020

(51) Int. Cl.
*A61M 16/10* (2006.01)
*A61M 16/06* (2006.01)
(Continued)

(52) U.S. Cl.
CPC .......... *A61M 16/105* (2013.01); *A61M 11/00* (2013.01); *A61M 16/0616* (2014.02); *A61M 16/1005* (2014.02); *G10L 25/51* (2013.01); *G10L 25/78* (2013.01); *H04R 1/08* (2013.01); *A61M 2202/0208* (2013.01)

(58) Field of Classification Search
CPC ............ A61M 16/105; A61M 16/0616; A61M 16/1005; A61M 16/104; A61M 16/1045; A61M 16/1055; A61M 16/106; A61M 16/1065; A61M 16/107; A61M 16/06; A61M 16/20; A61M 16/201; A61M 16/202; A61M 16/203; A61M 16/204; A61M 16/205; A61M 16/206; A61M 16/207; A61M 16/208; A61M 16/209; A61M 16/22; A61M 16/0078; A61M 16/0081; A61M 16/0084; A61M 11/00; A61M 11/002; A61M 11/006; A61M 11/007; A61M 11/008; A61M 2202/0208; G10L 25/51; G10L 25/78; H04R 1/08; H04R 1/083
See application file for complete search history.

(56) References Cited

U.S. PATENT DOCUMENTS

| 3,683,655 A | * | 8/1972 | White | A61H 31/00 |
| | | | | 601/44 |
| 4,951,661 A | * | 8/1990 | Sladek | A61M 16/0808 |
| | | | | 128/202.27 |

(Continued)

*Primary Examiner* — Joseph D. Boecker
*Assistant Examiner* — Brian T Khong
(74) *Attorney, Agent, or Firm* — Cooley LLP

(57) ABSTRACT

A device includes a body defining a respiration passage in fluidic communication with a filter fitting disposed on a first end of the body and a mask fitting disposed on a second end of the body, and a treatment passage in fluidic communication with the mask fitting. A treatment fitting is disposed on the body and is coupleable to a treatment source such that a seal in the treatment fitting transitions from a closed state to an open state to allow fluidic communication between the treatment source and the treatment passage. The device configured to permit (i) inhalation air and/or exhaled breath to be drawn and/or expelled through the filter fitting, the respiration passage, and the mask fitting and (ii) a respiratory therapeutic to be drawn from the treatment source coupled to the treatment fitting, through the treatment passage, and through the mask fitting.

30 Claims, 13 Drawing Sheets

(51) Int. Cl.
*A61M 11/00* (2006.01)
*G10L 25/51* (2013.01)
*G10L 25/78* (2013.01)
*H04R 1/08* (2006.01)

(56) References Cited

U.S. PATENT DOCUMENTS

| | | | |
|---|---|---|---|
| 6,606,994 B1* | 8/2003 | Clark | A61M 16/0808 128/204.18 |
| 6,609,515 B2 | 8/2003 | Bienvenu et al. | |
| 7,191,776 B2 | 3/2007 | Niles et al. | |
| 7,647,928 B2* | 1/2010 | Muellinger | A61M 15/00 128/206.22 |
| 7,841,335 B2 | 11/2010 | Harrington et al. | |
| 8,778,383 B2 | 7/2014 | Boucher et al. | |
| 10,130,786 B2* | 11/2018 | Pierro | A61M 11/06 |
| 10,335,558 B2 | 7/2019 | Boucher et al. | |
| 10,525,228 B2 | 1/2020 | Dhuper et al. | |
| 2001/0029950 A1* | 10/2001 | Haubeil | A61M 16/0078 128/205.13 |
| 2002/0162554 A1* | 11/2002 | Loescher | A61M 16/14 128/205.24 |
| 2005/0028811 A1* | 2/2005 | Nelson | A61M 16/06 128/200.11 |
| 2005/0217667 A1* | 10/2005 | Dhuper | A61M 15/0086 128/200.23 |
| 2006/0219243 A1* | 10/2006 | Walstrom | A61M 15/0086 128/201.13 |
| 2008/0251082 A1* | 10/2008 | Sinha | A61M 16/1065 128/207.16 |
| 2009/0260628 A1* | 10/2009 | Flynn, Sr. | A61M 16/0078 128/203.28 |
| 2009/0266357 A1* | 10/2009 | Varis | A61M 16/0858 128/202.27 |
| 2010/0122705 A1* | 5/2010 | Moenning, Jr. | A61M 16/104 128/206.24 |
| 2010/0252037 A1* | 10/2010 | Wondka | A61M 16/101 128/203.12 |
| 2010/0319687 A1* | 12/2010 | Esaki | A61M 11/06 128/200.23 |
| 2013/0061849 A1* | 3/2013 | Lemper | A61M 16/20 128/200.16 |
| 2013/0126011 A1* | 5/2013 | Abraham | A61M 16/08 137/315.01 |
| 2013/0327323 A1* | 12/2013 | Rubin | A61M 16/1055 128/200.18 |
| 2014/0128678 A1* | 5/2014 | Kileny | A61M 16/0816 600/114 |
| 2014/0190482 A1* | 7/2014 | Wade | A61M 16/122 128/203.25 |
| 2014/0196726 A1* | 7/2014 | Mallek | A61M 16/06 128/861 |
| 2014/0305431 A1* | 10/2014 | Holley | A61M 16/0003 128/201.13 |
| 2015/0114388 A1* | 4/2015 | Fernandez | A61M 16/0841 128/202.13 |
| 2015/0335852 A1* | 11/2015 | Miller | A61M 16/208 251/304 |
| 2015/0352299 A1* | 12/2015 | Cortez, Jr. | A61M 11/06 128/200.23 |
| 2016/0136368 A1* | 5/2016 | Spandorfer | A61M 16/14 128/201.13 |
| 2016/0228656 A1* | 8/2016 | Vasandani | A61M 15/0018 |
| 2017/0197052 A1* | 7/2017 | Tylka | A61M 16/0497 |
| 2020/0038618 A1* | 2/2020 | Ratner | A61M 16/209 |
| 2020/0154187 A1* | 5/2020 | Fukumoto | H04R 1/083 |
| 2020/0282173 A1* | 9/2020 | Yasinski | A61M 11/005 |
| 2020/0405989 A1* | 12/2020 | Farris | A61M 16/0808 |
| 2021/0023325 A1* | 1/2021 | Orth | A61M 16/0816 |

\* cited by examiner

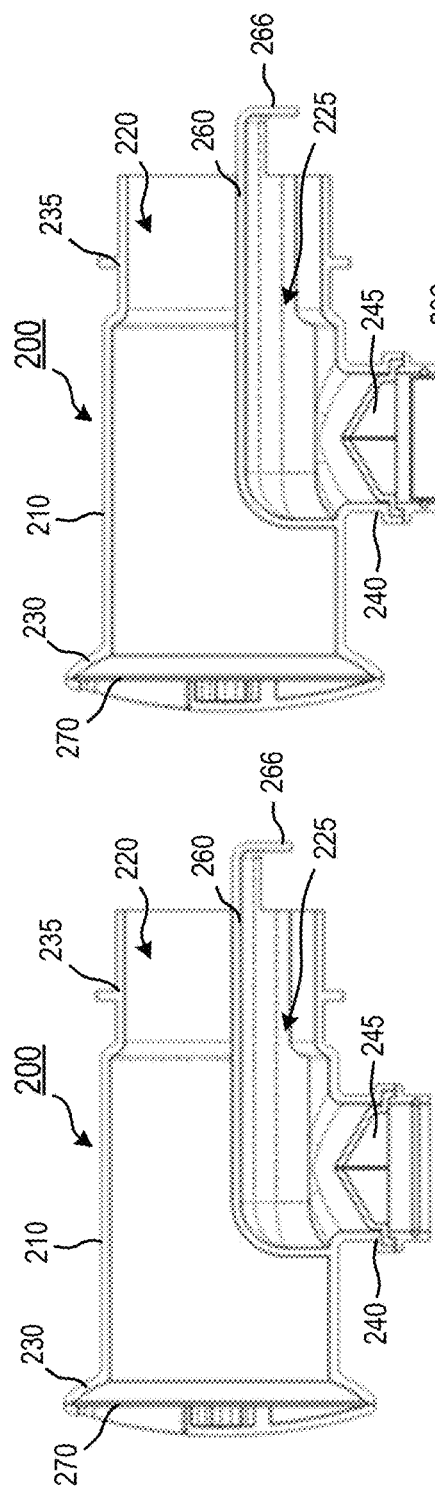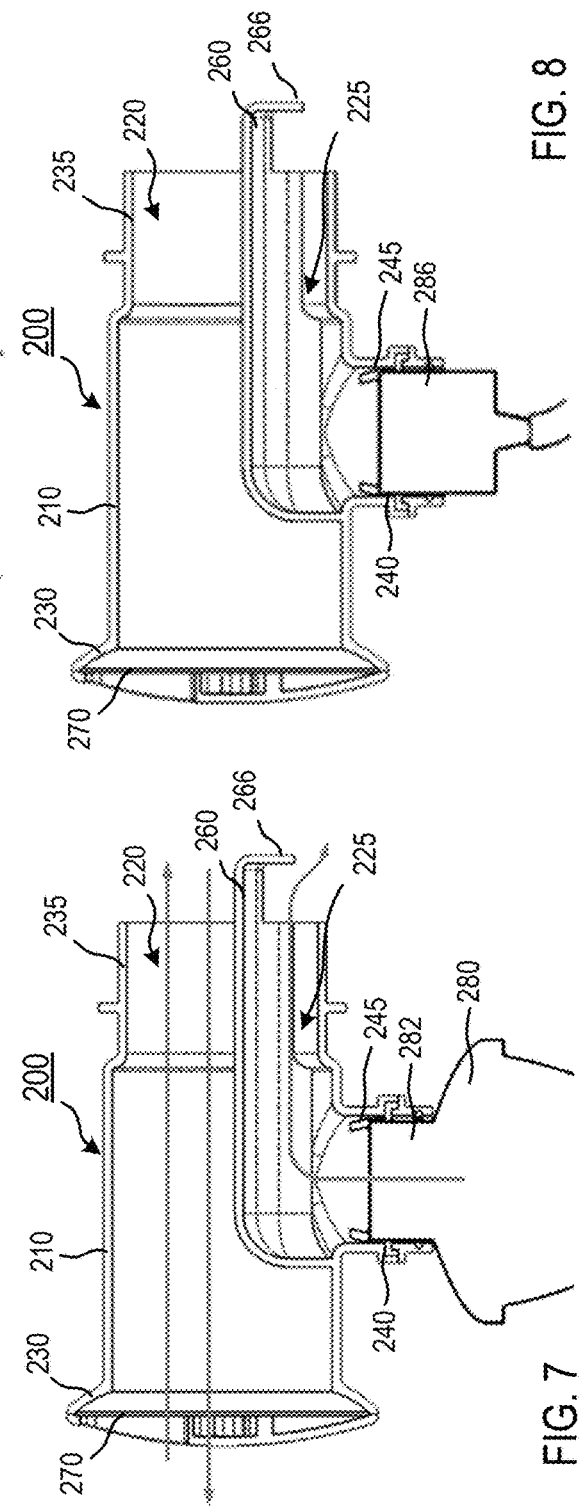

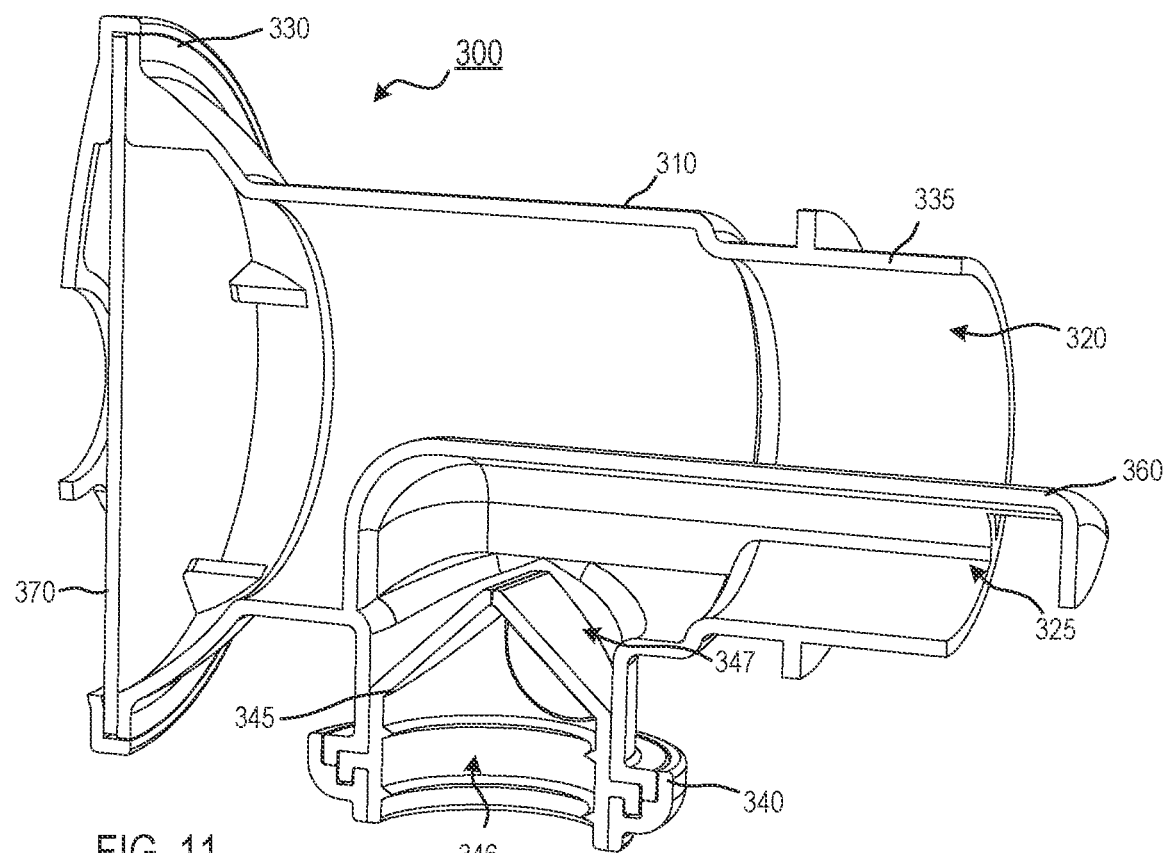
FIG. 11
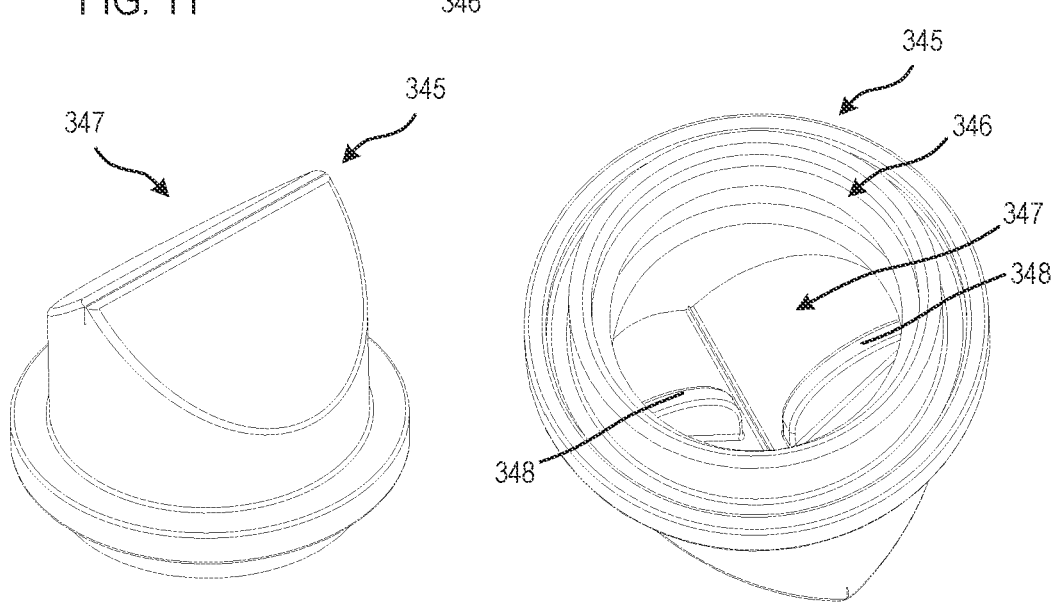
FIG. 12
FIG. 13

RESPIRATORY ISOLATION AND/OR TREATMENT DEVICES AND METHODS OF USING THE SAME

BACKGROUND

Embodiments described herein relate to respiratory isolation and/or treatment devices, and more particularly, to respiratory isolation and/or treatment device configured to provide respiratory treatment to a user while filtering inhalation air and exhaled breath through the device.

Supplemental oxygen, breathing treatments, nebulizer treatments, inhalers, etc. are a common method of treating respiratory conditions diseases such as asthma, pneumonia, cystic fibrosis, chronic obstructive pulmonary disease (COPD), bacterial, fungal, and/or viral respiratory infections, and/or the like. Breathing treatments may also be used to treat conditions such as sleep apnea and/or the like, and more generally, supplemental oxygen is commonly used in supportive care for those with cardiac issues, traumatic injuries, and in many other circumstances (e.g., chemical, biological, radiological, and nuclear defenses). In general, such treatments include the inhalation of therapeutics, air, oxygen ($O_2$), and/or any other suitable gaseous or aerosolized substance into the respiratory system of a user/patient, who then exhales normally.

Challenges exist, however, with providing effective respiratory treatments to patients who may also have an infectious disease such as bacterial, fungal, and/or viral respiratory infections such as, for example, the coronavirus leading to the COVID-19 disease. For example, it may be desirable to provide an isolated flow of a therapeutic to the patient to ensure proper and/or otherwise efficacious dosage or delivery of the therapeutic while simultaneously providing a separate flow path for inhalation and/or exhalation gasses that is filtered to prevent expelling contagions carried by the particles in exhaled breath. While certain known treatment devices may be configured to filter inhalation and exhalation gases as well as provide a respiratory therapeutic (and/or supplemental flow of $O_2$), such known devices fail to provide distinct, separate, and/or isolated flow paths, which can lead to decreased efficacy of the breathing treatment and/or an increased risk of expelling into the environment exhaled breath that may carry infectious contagions and/or the like.

Accordingly, a need exists for a respiratory isolation and/or treatment device configured to provide respiratory treatment, therapy, etc. to a user while filtering inhalation air and/or exhaled breath through the device.

SUMMARY

In some embodiments, a respiratory isolation and treatment device includes a body that defines a respiration passage extending through a first end and a second end of the body and a treatment passage extending through the second end of the body. A filter fitting is disposed on the first end of the body and is in fluidic communication with the respiration passage. A mask fitting is disposed on the second end of the body and is in fluidic communication with the respiration passage and the treatment passage. A treatment fitting is disposed on the body and is in selective fluidic communication with the treatment passage. A seal is disposed in the treatment fitting and is transitionable from a closed state to an open state in response to the treatment fitting being coupled to an output of a treatment source. The seal in the closed state substantially prevents fluid flow through the treatment fitting and into or out of the treatment passage. The seal in the open state allows fluidic communication between the treatment source and the treatment passage. The respiratory isolation and treatment device configured to permit (i) inhalation air to be drawn into the filter fitting, through the respiration passage, and out of the mask fitting, (ii) exhaled breath to be expelled into the mask fitting, through the respiration passage, and out of the filter fitting, and (iii) a gaseous or aerosolized treatment to be drawn from the output of the treatment source when coupled to the treatment fitting, through the treatment passage, and out of the mask fitting.

BRIEF DESCRIPTION OF THE DRAWINGS

FIG. 5 is a cross-sectional view of the device of FIG. 2 taken along the line A-A.

FIG. 6 is a cross-sectional view of the device of FIG. 2 taken along the line A-A and illustrating a treatment fitting of the device being coupled to a first treatment source according to an embodiment.

FIG. 7 is a cross-section view of the device and the first treatment source of FIG. 6 shown fully coupled and illustrating flow paths through at least a portion of the device.

FIG. 8 is a cross-section view of the device of FIGS. 5-7 shown with the treatment fitting fully coupled to a second treatment source according to an embodiment and illustrating flow paths through at least a portion of the device.

FIG. 11 is a cross-section view of the device of FIG. 9 taken along the line B-B.

FIGS. 12 and 13 are a top perspective view and a bottom perspective view of a seal configured to be disposed in a treatment fitting of the device shown in FIG. 11.

DETAILED DESCRIPTION

Figure 1:
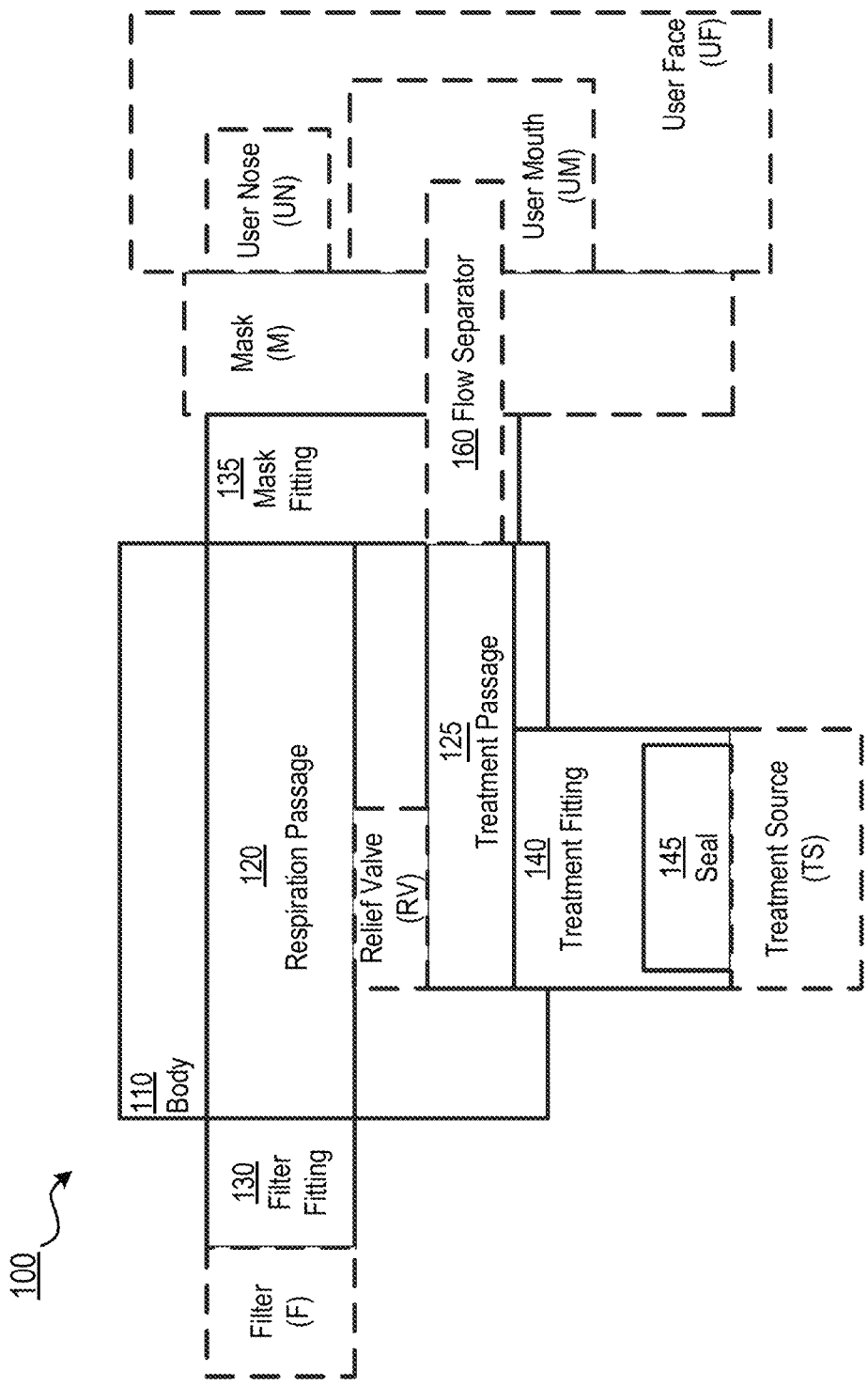
FIG. 1 is a schematic illustration of a respiratory isolation and treatment device according to an embodiment.
Figure 2:
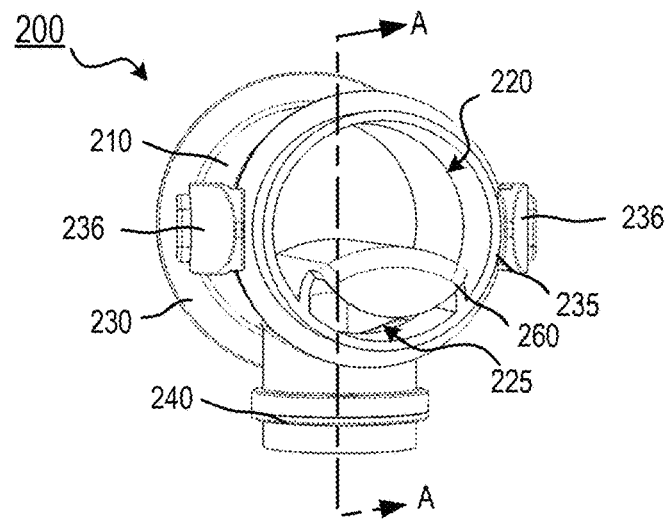
FIGS. 2-4 are various perspective views of a respiratory isolation and treatment device according to an embodiment.
Figure 3:
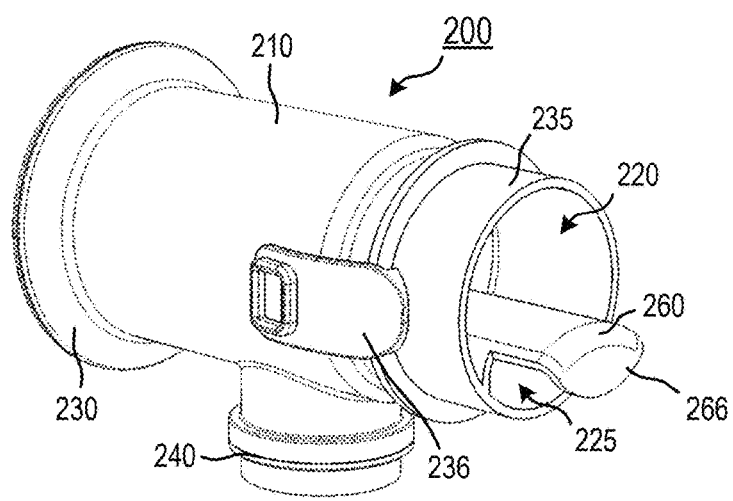

Embodiments and implementations described herein relate to respiratory isolation and treatment devices that can provide a user with respiratory treatment while filtering inhalation and exhaled breath through the device. In general, the respiratory isolation and treatment devices described herein can define at least two flow paths. A first flow path, for example, can be defined between a user of the respiratory isolation and treatment device (e.g., via a mask coupled to the device and worn by the user) and a filter coupled to a filter fitting of the device. A second flow path, separate from the first flow path, can be defined between the user (e.g., via the mask) and a treatment source coupled to the device. As such, the respiratory isolation and treatment device can allow a treatment such as air, oxygen-enriched air, therapeutic, and/or the like to be delivered from a treatment source to the user via the second flow path while restricting a flow of inhalation air and/or exhaled breath to a flow through the first flow path and the filter coupled to the filter fitting. Thus, the respiratory isolation and treatment device can be used to provide respiratory treatment to a user while limiting the spread of potential contagions that may be carried, for example, in the exhaled breath of the user.

In some embodiments, a respiratory isolation and treatment device includes a body that defines a respiration passage extending through a first end and a second end of the body and a treatment passage extending through the second end of the body. A filter fitting is disposed on the first end of the body and is in fluidic communication with the respiration passage. A mask fitting is disposed on the second end of the body and is in fluidic communication with the respiration passage and the treatment passage. A treatment fitting is disposed on the body and is in selective fluidic communication with the treatment passage. A seal is disposed in the treatment fitting and is transitionable from a closed state to an open state in response to the treatment fitting being coupled to an output of a treatment source. The seal in the closed state substantially prevents fluid flow through the treatment fitting and into or out of the treatment passage. The seal in the open state allows fluidic communication between the treatment source and the treatment passage. The respiratory isolation and treatment device is configured to permit (i) inhalation air to be drawn into the filter fitting, through the respiration passage, and out of the mask fitting, (ii) exhaled breath to be expelled into the mask fitting, through the respiration passage, and out of the filter fitting, and (iii) a gaseous or aerosolized treatment to be drawn from the output of the treatment source when coupled to the treatment fitting, through the treatment passage, and out of the mask fitting.

In some embodiments, a respiratory isolation and treatment device includes a body that defines a respiration passage extending through a first end and a second end of the body and a treatment passage extending through the second end of the body. A filter fitting is disposed on the first end of the body and is in fluidic communication with the respiration passage. The filter fitting is removably coupleable to a high-efficiency particulate air (HEPA) filter such that fluid flow through the first end of the body passes through the HEPA filter when coupled to the filter fitting. A mask fitting is disposed on the second end of the body. A first portion of the mask fitting is in fluidic communication with the respiration passage and a second portion of the mask fitting is in fluidic communication with the treatment passage. A treatment fitting is disposed on the body and is in selective fluidic communication with the treatment passage. The treatment fitting has a seal disposed therein that is transitionable from a closed state to an open state in response to the treatment fitting being coupled to an output of a treatment source. The seal in the closed state substantially prevents fluid flow through the treatment fitting and into or out of the treatment passage. The seal in the open state allows fluidic communication between the treatment source and the treatment passage. The respiratory isolation and treatment device is configured to permit substantially contemporaneous bidirectional fluid flow through the respiration passage between the filter fitting and the first portion of the mask fitting and unidirectional fluid flow through the treatment passage from the treatment fitting and to the second portion of the mask fitting.

In some embodiments, a respiratory isolation and treatment device can be included in a kit including a sealable packaging, at least one filter removably disposed in the packaging, and the respiratory isolation and treatment device removably disposed in the packaging. The respiratory isolation and treatment device includes a body defining a respiration passage extending through a first end and a second end of the body and a treatment passage extending through the second end of the body. The respiratory isolation and treatment device further includes a filter fitting disposed on the first end of the body and in fluidic communication with the respiration passage, a mask fitting disposed on a second end of the body and in fluidic communication with the respiration passage and the treatment passage, and a treatment fitting disposed on the body and in selective fluidic communication with the treatment passage. The treatment fitting has a seal that is in a closed state when the respiratory isolation and treatment device is disposed in the packaging such that a flow of fluid through the treatment fitting is substantially prevented and that is transitionable to an open state when the respiratory isolation and treatment device is outside of the packaging and the treatment fitting is coupled to an output of a treatment source to establish fluidic communication between the treatment source and the treatment passage. The at least one filter is configured to removably couple to the filter fitting.

In some implementations, a method of using a respiratory isolation and treatment device to deliver a gaseous or aerosolized treatment and/or therapeutic can include coupling a filter to a filter fitting disposed on a first end of a body of the respiratory isolation and treatment device. The body of the device defines a respiration passage extending through the first end and a second end of the body and a treatment passage extending through the second end of the body. The filter fitting is in fluidic communication with a respiration passage defined by the body. The filter fitting and the filter collectively form a fluidic seal such that fluid flow through the first end of the body is through the filter fitting and the filter coupled thereto. A mask fitting disposed on a second end of the body and in fluidic communication with the respiration passage is coupled to a port of a mask. The mask is secured to a user such that (i) an edge portion of the mask is placed against the face of the user, (ii) the mask covers at least the nostrils and the mouth of the user, and (iii) the mask fitting is at least partially aligned with the mouth of the user. An output of a treatment source is coupled to a treatment fitting disposed on the body and in fluidic communication with the treatment passage. A seal disposed in the treatment fitting is transitioned from a closed state to an open state in response to coupling the treatment fitting to the output of the treatment source and a flow of a gaseous or aerosolized treatment and/or therapeutic is provided through the treatment passage from the treatment source to the mouth of the user. A bidirectional flow of fluid is allowed between the user and a volume outside of the device via the respiration passage, the filter fitting, and the filter coupled thereto, where the bidirectional flow of fluid is separate from the flow of the gaseous or aerosolized treatment and/or therapeutic provided to the user.

The terminology used herein is for the purpose of describing particular embodiments only and is not intended to limit the full scope of the claims. Unless defined otherwise, all technical and scientific terms used herein have the same meanings as commonly understood by one of ordinary skill in the art.

As used in this specification, the singular forms "a," "an," and "the" include plural referents unless the context clearly dictates otherwise. For example, the term "a member" is intended to mean a single member or a combination of members, "a material" is intended to mean one or more materials, or a combination thereof. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims, are generally intended as "open" terms (e.g., the term "including" should be interpreted as "including but not limited to," the term "having" should be interpreted as "having at least," etc.). For example, the terms "comprise(s)" and/or "comprising," when used in this specification, are intended to mean "including, but not limited to." While such open terms indicate the presence of stated features, integers (or fractions thereof), steps, operations, elements, and/or components, they do not preclude the presence or addition of one or more other features, integers (or fractions thereof), steps, operations, elements, components, and/or groups thereof, unless expressly stated otherwise.

As used herein the term "and/or" includes any and all combinations of one or more of the associated listed items. Said another way, the phrase "and/or" should be understood to mean "either or both" of the elements so conjoined (i.e., elements that are conjunctively present in some cases and disjunctively present in other cases). It should be understood that any suitable disjunctive word and/or phrase presenting two or more alternative terms, whether in the description, claims, or drawings, contemplate the possibilities of including one of the terms, either of the terms, or both terms. Other elements may optionally be present other than the elements specifically identified by the "and/or" clause, whether related or unrelated to those elements specifically identified. Thus, as a non-limiting example, a reference to "A and/or B" can refer to "A" only (optionally including elements other than "B"), to "B" only (optionally including elements other than "A"), to both "A" and "B" (optionally including other elements), etc.

As used herein, "or" should be understood to have the same meaning as "and/or" as defined above. For example, when separating items in a list, "or" or "and/or" shall be interpreted as being inclusive (e.g., the inclusion of at least one, but also including more than one, of a number or list of elements, and, optionally, additional unlisted items). Only terms clearly indicated to the contrary, such as when modified by "only one of" or "exactly one of" (e.g., only one of "A" or "B," "A" or "B" but not both, and/or the like) will refer to the inclusion of exactly one element of a number or list of elements.

As used herein, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements, unless expressly stated otherwise. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B" or "at least one of A and/or B") can refer to one or more "A" without "B," one or more "B" without "A," one or more "A" and one or more "B," etc.

All ranges disclosed herein are intended to encompass any and all possible subranges and combinations of subranges thereof unless expressly stated otherwise. Any listed range should be recognized as sufficiently describing and enabling the same range being broken down into at least equal subparts unless expressly stated otherwise. As will be understood by one skilled in the art, a range includes each individual member and/or a fraction of an individual member where appropriate.

As used herein, the terms "about," "approximately," and/or "substantially" when used in connection with stated value(s) and/or geometric structure(s) or relationship(s) is intended to convey that the value or characteristic so defined is nominally the value stated or characteristic described. In some instances, the terms "about," "approximately," and/or "substantially" can generally mean and/or can generally contemplate a value or characteristic stated within a desirable tolerance (e.g., plus or minus 10% of the value or characteristic stated). For example, a value of about 0.01 can include 0.009 and 0.011, a value of about 0.5 can include 0.45 and 0.55, a value of about 10 can include 9 to 11, and a value of about 100 can include 90 to 110. Similarly, a first surface may be described as being substantially parallel to a second surface when the surfaces are nominally parallel. While a value, structure, and/or relationship stated may be desirable, it should be understood that some variance may occur as a result of, for example, manufacturing tolerances or other practical considerations (such as, for example, the pressure or force applied through a portion of a device, conduit, lumen, etc.). Accordingly, the terms "about," "approximately," and/or "substantially" can be used herein to account for such tolerances and/or considerations.

As used herein, the term "set" can refer to multiple features or a singular feature with multiple parts. For example, when referring to a set of walls, the set of walls can be considered as one wall with multiple portions, or the set of walls can be considered as multiple, distinct walls. Thus, a monolithically constructed item can include a set of walls. Such a set of walls may include multiple portions that are either continuous or discontinuous from each other. A set of walls can also be fabricated from multiple items that are produced separately and are later joined together (e.g., via a weld, an adhesive, or any suitable method).

As used herein, the term "fluid" can refer to any suitable liquid substance, gaseous substance, and/or any suitable mixture or combination thereof. As such, the term "fluid" can refer to a liquid such as water, liquid medicament, liquid therapeutic, bodily fluid (e.g., spittle, blood, mucus, airway surface liquid (ASL), etc.; a gas such as air, oxygen ($O_2$), nitric oxide (NO), nitrous oxide ($N_2O$) or other anesthetic gases, etc.; and or mixtures or combinations thereof such as, for example, aerosolized medicaments, therapeutics, treatments, etc., nebulized medicaments, therapeutics, treatments, etc., and/or the like. As described in further detail herein, any of the devices described herein can be configured to provide any number of flow paths configured to receive a flow of fluid such as, for example, inhalation air; exhaled breath; treatment fluids or gasses (e.g., air, $O_2$, etc.); gaseous, aerosolized, and/or nebulized therapeutics; and/or the like or combinations thereof. Unless expressly stated otherwise, reference to a particular fluid (e.g., a gas) is not intended to be to the exclusion of any other fluid particles that may be included in and/or carried by that fluid (e.g., a gas such as air that may be carrying aerosolized particles).

The embodiments described herein and/or portions thereof can be formed or constructed of one or more biocompatible materials. In some embodiments, the biocompatible materials can be selected based on one or more properties of the constituent material such as, for example, stiffness, toughness, durometer, bioreactivity, etc. Examples of suitable biocompatible materials include but are not necessarily limited to polymers, metals, glasses, and/or ceramics\. A polymer material may be biodegradable or non-biodegradable. Examples of suitable biodegradable polymers include polylactides, polyglycolides, polylactide-co-glycolides, polyanhydrides, polyorthoesters, polyetheresters, polycaprolactones, polyesteramides, poly(butyric acid), poly(valeric acid), polyurethanes, biodegradable polyamides (nylons), and/or blends and copolymers thereof. Examples of non-biodegradable polymers include non-degradable polyamides (nylons), polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, and/or blends and copolymers thereof. Examples of suitable metals include pharmaceutical grade stainless steel, gold, titanium, nickel, iron, platinum, tin, chromium, copper, and/or alloys thereof.

Referring now to the drawings, FIG. 1 is a schematic illustration of a respiratory isolation and treatment device 100 according to an embodiment. The respiratory isolation and treatment device 100 (also referred to herein as "device") can be any suitable shape, size, and/or configuration. In some embodiments, for example, the device 100 can be configured for use in any number of settings and adapted to receive, engage, couple to, and/or otherwise function with one or more devices such as masks, hoods, shields, therapeutic and/or oxygen delivery devices, filters, resuscitators, and/or the like. In other embodiments, the device 100 can include and/or can be integral with any such device.

As shown, the device 100 includes a body 110, a filter fitting 130 disposed at a first end of the body 110, a mask fitting 135 disposed at a second end of the body 110, and a treatment fitting 140. The body 110 defines a respiration passage 120 extending through and/or otherwise passing between the first end and the second end of the body 110. More particularly, the respiration passage 120 extends through the body 110 and is in fluidic communication with each of the filter fitting 130 disposed at the first end of the body 110 and the mask fitting 135 (or at least a portion thereof) disposed at the second end of the body 110. The body 110 also defines a treatment passage 125 that extends through at least a portion of the body 110. More particularly, the treatment passage 125 extends through at least a portion of the body 110 and is in fluidic communication with each of the treatment fitting 140 and the mask fitting 135 disposed at the second end of the body 110. The arrangement of the body 110 is such that the respiration passage 120 and the treatment passage 125 provide and/or define separated, isolated, distinct, and/or otherwise independent flow paths through at least a portion of the body 110, as described in further detail herein.

The body 110 can be any suitable shape, size, and/or configuration, and can be formed from any suitable material such as one or more of the biocompatible materials described above. For example, the body 110 can be substantially cylindrical with its first end and its second end being substantially open. In other embodiments, the body 110 can be polygonal, oblong, substantially irregular, and/or the like. In some embodiments, the size and/or shape of the body 110 is based at least in part on a desired size, shape, diameter, etc. of the respiration passage 120 and/or the treatment passage 125 at least partially extending therethrough. For example, the body 110 can be substantially annular with an inner surface that defines an inner volume. A first portion of the inner volume can form the respiration passage 120 and a second portion of the inner volume—separate and/or at least partially isolated from the first portion of the inner volume—can form the treatment passage 125. As such, the size, shape, and/or configuration of the body 110 can be based at least in part on one or more desired characteristics of at least the respiration passage 120 and/or the treatment passage 125. The desired characteristics can be, for example, size, shape, diameter, pressure rating, expected and/or desired flow rates through each of the passages 120 and/or 125, and/or any other suitable characteristics.

Similarly, the inner surface of the body 110 (e.g., that defines the inner volume) can be and/or can include any suitable shape, feature, coating, etc. configured to facilitate a desired flow of fluid through the respiration passage 120 and/or the treatment passage 125. For example, in some embodiments, one or more portions of the inner surface of the body 110 can include a coating or surface treatment such as a hydrophobic coating, a hydrophilic coating, an antimicrobial coating, an antiviral coating, an antifungal coating, and/or the like. In some embodiments, one or more portions of the inner surface of the body 110 can include one or more surface features such as pit(s), groove(s), channel(s), ridge(s), rib(s), protrusion(s), etc. that can be configured to facilitate, direct, hinder, and/or otherwise affect fluid flow through at least a portion of the body 110. For example, the inner surface can include one or more features configured to diffuse fluid particles and/or increase a turbulence of associated with a fluid flow through a portion of the body 110, one or more features configured to facilitate a substantially uniform, consistent, and/or laminar fluid flow through a portion of the body 110, and/or any suitable combination of such features.

The filter fitting 130 of the device 100 is disposed on or at the first end of the body 110. The filter fitting 130 can be coupled to the first end of the body 110 or can be integrally formed with the first end of the body 110. That is to say, the filter fitting 130 can be independent of the body 110 and coupled to the first end thereof (e.g., during manufacturing) or can be formed by and/or otherwise integral with the body 110 (e.g., unitarily or monolithically formed). The filter fitting 130 can define an opening that is aligned with and/or otherwise in fluid communication with the respiration passage 120 such that a flow of fluid into or out of the first end of the body 110 passes through the opening.

The filter fitting 130 is configured to be removably coupled to a filter F. In some embodiments, a portion of the filter fitting 130 can receive a portion of the filter F, which can be at least temporarily maintained in a substantially fixed position via a friction or interference fit. In other embodiments, the filter F and the filter fitting 130 can collectively form a threaded coupling, a press fit, a snap fit, and/or any other suitable removable coupling. In some implementations, removably coupling the filter F to the filter fitting 130 can allow the filter F to be replaceable. For example, it may be desirable to replace the filter F after each use of the device 100. In some implementations, it may be desirable to replace a filter F before or at a predetermined expiration or date at which the filter F begins to lose efficacy; if a filter F becomes damaged, torn, ripped, or broken; if a filter F becomes damp, wet, and/or saturated; and/or the like.

The filter F can be any suitable filter configured to provide a desired level of particulate filtration. For example, the filter F can be, for example, a high efficiency particulate air (HEPA) filter, a N-95 filter, a N-99 filter, a N-100 filter, and/or any other suitable filter. In some implementations, the filter F can be any suitable filter meeting or exceeding a standardized guideline such as, for example, the Center for Disease Control (CDC) Guidelines for Isolation Precautions in Hospitals (e.g., at least a N-95 filter), and/or the like. In some implementations, the filter F can be at least partially resistant to oil such as, for example, an R-95 filter, an R-99 filter, an R-100 filter, etc., or can be substantially oil proof such as, for example, a P-95 filter, a P-99 filter, a P-100 filter, etc. In some implementations, the filter F can be a filter suitable for use in chemical, biological, radiological, and/or nuclear defense response situations (e.g., military, governmental, and/or civilian use).

The filter F is removably coupleable to the filter fitting 130 such that the filter F is aligned with, obstructs, and/or otherwise covers the opening defined by the filter fitting 130. Moreover, a portion of the filter F can form a substantially fluid-tight seal with a portion or surface of the filter fitting 130 that surrounds or is outside of the opening. Thus, when the filter F is coupled to the filter fitting 130, substantially all fluid flow through the first end of the body 110 flows through the opening of the filter fitting 130 and the filter F covering the opening. In some implementations, the arrangement of the filter fitting 130 and one or more filters F can be such that during replacement of a filter F, the opening defined by the filter fitting 130 is aligned with or covered by at least one of the original filter F or the replacement filter F. For example, during replacement, a portion of each filter F can form a substantially fluid-tight seal around the opening such that substantially all flow into or out of the first end of the body 110 passes through the opening of the filter fitting 130 and at least one of the original filter F and/or the replacement filter F, as described in further detail herein with reference to specific embodiments.

The mask fitting 135 of the device 100 is disposed on or at the second end of the body 110. The mask fitting 135 can be coupled to the second end of the body 110 or can be integrally formed with the second end of the body 110. That is to say, the mask fitting 135 can be independent of the body 110 and coupled to the second end thereof (e.g., during manufacturing) or can be formed by and/or otherwise integral with the body 110 (e.g., unitarily or monolithically formed). The mask fitting 135 can define at least one opening that is aligned with and/or otherwise in fluid communication with the respiration passage 120 and/or the treatment passage 125 such that a flow of fluid into or out of the second end of the body 110 passes through the at least one opening. For example, the mask fitting 135 can define a first opening in fluid communication with the respiration passage 120 and a second opening in fluid communication with the treatment passage 125. Said another way, the respiration passage 120 can extend through a first portion of the mask fitting 135 and the treatment passage 125 can extend through a second portion of the mask fitting 135 that is different from the first portion of the mask fitting 135.

The mask fitting 135 is configured to be removably coupled to a mask M. In some embodiments, the mask fitting 135 can be and/or can form a port that is configured to be coupled to a corresponding port on some known masks. In other embodiments, the mask fitting 135 can be configured to couple to a specifically designed port or coupling portion of a mask M. In some embodiments, a portion or port of the mask M can receive at least a portion of the mask fitting 135, which can at least temporarily couple the device 100 to the mask M. In some embodiments, the portion or port of the mask M and the portion or port of the mask fitting 135 can collectively form a friction fit, an interference fit, a press fit, a snap fit, a threaded coupling, and/or any other suitable coupling. In some embodiments, the mask fitting 135 can include one or more couplers (e.g., tabs, arms, latches, etc.) configured to at least temporarily engage a portion of the mask M, thereby coupling the device 100 to the mask M. In other embodiments, the mask fitting 135 can be fixedly coupled to a mask M (e.g., during manufacturing). In such embodiments, the device 100 and the mask M (with or without one or more filters F) can be packaged together and sold, for example, as a kit or the like.

As shown in FIG. 1, the mask M can be donned by a user such that (i) an edge surface of the mask M is in contact with the user's face UF and (ii) the mask M substantially covers the user's nose UN and the user's mouth UM. For example, the mask M can include a set of one or more straps, rings or loops (e.g., with a tightening mechanism, snaps, and/or ratchet), arm/hooks, and/or any other suitable attachment mechanism that can be placed around at least a portion of the user's head to temporarily couple the mask M to the user's head and/or face. The mask fitting 135 can be at least partially aligned with the user's mouth UM and/or the user's nose UN when the mask M is donned by the user. In some implementations, donning the mask M can be such that the contact between the edge surface of the mask M and the user's face UF forms a substantially fluid-tight seal. As such, when the user dons the mask M, respiration air passes between the user's respiratory system and a volume outside of the mask M via a port, coupler, connector, adapter, and/or portion to which the mask fitting 135 is at least temporarily coupled. Furthermore, with the respiration passage 120 in fluid communication with each of the filter fitting 130 and the mask fitting 135, the coupling of the filter fitting 130 to the filter F and the coupling of the mask filter 135 to the mask M is such that respiration air (e.g., inhalation air and exhaled breath) to and/or from the user donning the mask M passes through the respiration passage 120 of the device 100 and the filter F coupled to the filter fitting 130. Thus, the filter F can filter the inhalation air drawn into the device 100, which protects the user from contaminants in the air, and can filter the exhaled breath expelled by the user, which protects others from contaminants in the exhaled breath (e.g., bacterial and/or viral aerosols carried by the exhaled breath).

The treatment fitting 140 of the device 100 is disposed on or along a portion or end of the body 110 and is in fluid communication with the treatment passage 125. As described above with reference to the filter fitting 130 and the mask fitting 135, the treatment fitting 140 can be coupled to the body 110 or can be integrally formed with the second end of the body 110. That is to say, the treatment fitting 140 can be independent of the body 110 and coupled to a portion, side, or end thereof (e.g., during manufacturing) or can be formed by and/or otherwise integral with the body 110 (e.g., unitarily or monolithically formed).

As shown in FIG. 1, for example, the treatment fitting 140 can be disposed on or along a side of the body 110 between the first end and the second end thereof. In other embodiments, the treatment fitting 140 can be disposed on or at the first end of the body 110 or the second end of the body 110. In some embodiments, the treatment fitting 140 can be arranged in a substantially perpendicular orientation relative to at least one of the filter fitting 130 and/or the mask fitting 135. For example, a first axis can extend through each of the filter fitting 130 and the mask fitting 135 and a second axis perpendicular or orthogonal to the first axis can extend through the treatment fitting 140. In other embodiments, the treatment fitting 140 can be disposed at any suitable orientation relative to the filter fitting 130 and/or mask fitting 135. For example, each of the filter fitting 130 and the treatment fitting 140 can be disposed on or at the first end of the body 110 and arranged in a Y-shaped configuration relative to the mask fitting 135 (e.g., the first end of the body 110 can form a Y-shaped bifurcation with the filter fitting 130 disposed on a first "branch" of the bifurcation and the treatment fitting 140 disposed on a second "branch" of the bifurcation).

The treatment fitting 140 is configured to be removably coupled to inlet gas source and/or treatment source (TS), which might be oxygen-enriched air, nebulized medication or other gas mixtures to include anesthetics. In some embodiments, the treatment fitting 140 can be and/or can form a port that is configured to be coupled to a corresponding port or outlet of a treatment source TS. In some embodiments, the treatment fitting 140 can receive at least a portion of the output of a treatment source TS to at least temporarily couple the treatment source TS to the body 110 of the device 100. In some embodiments, the treatment fitting 140 and at least a portion of the treatment source TS can collectively form a friction fit, an interference fit, a press fit, a snap fit, a threaded coupling, and/or any other suitable coupling. In some embodiments, the treatment fitting 140 can include one or more couplers (e.g., tabs, arms, latches, etc.) configured to at least temporarily engage the portion of the treatment source TS, thereby coupling the treatment source TS to the device 100. In other embodiments, the treatment fitting 140 can be fixedly coupled to the treatment source TS (e.g., during manufacturing). In such embodiments, the respiratory isolation and treatment device 100 and the treatment source TS (e.g., with or without one or more filters or masks) can be packaged together and sold, for example, as a single use kit or the like.

The treatment fitting 140 can be used with and/or at least temporarily coupled to any suitable treatment source TS. In some implementations, for example, a treatment source TS can be a device configured to deliver a gaseous or aerosolized treatment, therapeutic, medicament, and/or the like. Such a device can be a nebulizer or the like. In some implementations, the treatment source TS can be an outlet of a reservoir, tank, canister, etc. containing a pressurized fluid such as air, oxygen ($O_2$), nitric oxide (NO), nitrous oxide ($N_2O$) or other anesthetic gases, and/or any other suitable fluid (e.g., gas) or combination of fluids. In some implementations, the therapeutic can be oxygen enriched air. For example, the therapeutic can be room air having a fraction of inspired oxygen ($FiO_2$) of about 21% or can be oxygen enriched air having an $FiO_2$ of about 22%, 25%, 30%, 35%, 40%, 45%, 50%, 55%, 60%, 65%, 70%, 75%, 80%, 85%, 90%, 95%, 99%, or 100% or any percentage of fraction of a percent therebetween. In some implementations, the treatment source TS can be a manual resuscitator such as an AMBU® bag and/or the like.

As shown in FIG. 1, the treatment fitting 140 includes a seal 145 configured to selectively engage the treatment source TS when coupled to the treatment fitting 140. The seal 145 can be any suitable seal, valve, port, etc. In some embodiments, the seal 145 can include multiple seals or portions configured to selectively engage a portion of the treatment source TS when coupled to the treatment fitting 140. For example, the seal 145 can include a first seal or portion configured to contact a portion of the treatment source TS to form a substantially fluid tight seal therebetween. The seal 145 can also include a seal, valve, or portion configured to transition between a closed state or configuration and an open state or configuration. The seal 145, for example, can be disposed within the treatment fitting 140 between the treatment passage 125 and an outer opening of the treatment fitting 140. In the closed state, the seal 145 creates substantial fluidic isolation through the treatment fitting 140 between the treatment passage 125 and a volume outside of the body 110 of the respiratory isolation and treatment device 100. Conversely, in the open state, the seal 145 can establish fluid communication through treatment fitting 140 allowing the treatment passage 125 to be placed in fluid communication with, for example, a treatment source TS coupled to the treatment fitting 140.

In some implementations, the seal 145 or a portion thereof can be transitioned from the closed state (e.g., a first configuration) to the open state (e.g., a second configuration) in response to physical contact with a portion of the treatment source TS when coupled to the treatment fitting 140. In some implementations, the seal 145 can be transitioned in response to a pressure differential across the seal 145 (e.g., a pressure differential with a magnitude greater than a "cracking" pressure of the seal 145 or valve portion thereof). For example, in some instances, a treatment source TS can include a therapeutic that is under pressure, which in turn, can exert a positive pressure on a portion of the seal 145 operable to transition the seal 145 (or valve portion thereof) from the closed state to the open state. In other instances, the treatment source TS can be coupled to the treatment fitting 140 and the seal 145 can be transitioned from the closed state to the open state in response to a negative pressure on a portion of the seal 145 as a result of inhalation by the user (e.g., resulting in a suction force through at least the treatment passage 125).

In some implementations, the seal 145 can be and/or can include a one-way valve that allows a flow of fluid through the valve in a single direction. For example, the seal 145 can be configured to allow a flow of fluid from the treatment source coupled to the treatment fitting 140, into and through the treatment passage 125, and out a portion of the mask fitting 135 at or on the second end of the body 110. Conversely, the seal 145 can be configured to prevent a flow of fluid from the treatment passage 125, into and/or through the treatment fitting 140, and through or past the seal 145 (e.g., out into the environment surrounding the device 100). In this manner, the body 110 of the device 100 and the seal 145 can prevent a flow of fluid (e.g., exhaled breath) that may be carrying aerosolized infectious particles from exiting the device 100 through a portion other than the filter fitting 130 and the filter F coupled thereto, as described above. In other words, the arrangement of the treatment fitting 140, the seal 145, and the treatment passage 125 is such that a substantially unidirectional flow of fluid can pass through the device 100 via the treatment passage 125.

As shown in FIG. 1, the respiratory isolation and treatment device 100 optionally may include a flow separator 160 disposed on or at the second end of the body 110. In some embodiments, the flow separator 160 is at least partially disposed in the body 110 and is configured to physically and fluidically separate the respiration passage 120 from the treatment passage 125. Said another way, the flow separator 160 can be at least partially disposed in the body 110 and can include or form a wall having a first surface that defines a portion of the respiration passage 120 and a second surface, opposite the first surface, that defines a portion of the treatment passage 125.

In some embodiments, a portion of the flow separator 160 extends beyond the second end of the body 110 and through or beyond the mask fitting 135. As shown in FIG. 1, for example, the flow separator 160 can extend through the mask fitting 135 and into or through the mask M coupled thereto. In some embodiments, the flow separator 160 can extend a sufficient distance to allow a portion of the flow separator 160 to be inserted and/or otherwise disposed in the user's mouth UM when the mask fitting 135 is connected to the mask M and the mask M is donned by the user. In other embodiments, the flow separator 160 only extends into the mask M slightly such that it is not inserted and/or disposed in the user's mouth UM during use. In some embodiments, the flow separator 160 can have a telescoping configuration allowing the flow separator 160 to be transitioned between a first configuration having a first length and a second configuration having a second length longer than the first length. In such embodiments, telescoping the flow separator 160 from the first configuration to the second configuration can increase a length of the flow separator 160 a sufficient amount to allow a portion of the flow separator 160 to be inserted and/or disposed in the user's mouth UM when in the second configuration.

In some embodiments, the flow separator 160 is substantially hollow and at least partially defines or is in fluid communication with the treatment passage 125. The flow separator 160 can be configured to at least partially direct and/or control a flow of fluid between the treatment passage 125 and the user donning the mask M. For example, a portion of the flow separator 160 can be disposed in the user's mouth UM when the user dons the mask M and thus, can direct a flow of fluid from the treatment source TS coupled to the treatment fitting 140 into the user's mouth UM. In some embodiments, the flow separator 160 can have an end portion configured to at least partially direct a flow of fluid. For example, the end portion of the flow separator 160 can be bent, curved, and/or at least partially closed to direct a flow of flow in a desired direction such as, for example, downward and/or otherwise away from the portion of the mask fitting 135 in fluid communication with the respiration passage 120. As such, the flow separator 160 can reduce and/or limit a mixing of the flow of fluid (e.g., a gaseous or aerosolized treatment, therapeutic, and/or medicament; gasses such as air, oxygen, nitric oxide, nitrous oxide or other anesthetic gases, and/or the like; and/or any other suitable fluid) being delivered to the user via the treatment passage 125 with a flow of fluid being passed between the user and the respiration passage 120 (e.g., inhalation air and/or exhaled breath), which in some instances, may otherwise decrease a therapeutic effect of the fluid being delivered via the treatment passage 125.

As described above, the device 100 can be used to deliver a respiratory treatment, therapy, etc. to a user while simultaneously filtering the exchange of respiratory air between the user and the environment outside of the device 100, thereby reducing a potential risk of exposing the user and/or others to undesirable aerosols such as infectious viral or bacterial particles, as well as chemical or radioactive toxins. Specifically, in use, the mask fitting 135 can be coupled to the mask M (e.g., any suitable mask, hood, shield, etc.) and a filter F can be coupled to the filter fitting 130. When the mask M is donned by the user, the respiration passage 120 of the device 100 provides a dedicated, bidirectional flow path between the user and the filter F allowing for the exchange of filtered inhalation air and/or filtered exhaled breath between the user and the environment outside of the device 100. In a substantially simultaneous process, the treatment passage 125 provides an independent, separated, isolated, and/or dedicated flow path between the treatment source TS coupled to the treatment fitting 140 and the user donning the mask M, allowing for the delivery of a respiratory treatment, therapy, etc. In some implementations, the flow path through the treatment passage 125 is a unidirectional flow path in a direction to and/or toward the user (e.g., allowing flow from the treatment source TS coupled to the treatment fitting 140 to and/or toward the user). As such, the device 100 can be used to deliver respiratory treatment and/or therapy to a user who may, for example, have an infectious or contagious condition or disease such as, for example, the coronavirus leading to the COVID-19 disease while reducing, limiting, and/or mitigating a risk of spreading the condition or disease, for example, via aerosolized particles carried by the user's exhaled breath.

Although not shown in FIG. 1, in some embodiments, the device 100 and/or the mask M coupled to the device 100 can include a communication system configured to facilitate communication with user of the device 100. For example, in some instances, it may be difficult to hear and/or understand a user donning a mask, hood, and/or the like. In such instances, the communication system can include, for example a microphone, microprocessor and filtering software disposed in the mask (or hood) and/or in a portion of the body 110 of the device 100, which can "pick-up" sounds associated with the user's speech and transmit audio data to a speaker configured to transmit the audio data. In some implementations, the speaker can be wired to the microphone and coupled to and/or integrated with the mask and/or body 110 of the device 100. In other implementations, the microphone can be in wireless communication with a speaker via any suitable wireless network (e.g., Wi-Fi®, Bluetooth®, Near Field Communication (NFC), Z-Wave®, Zigbee®, and/or any other suitable).

In some implementations, the communication system can also include, for example, one or more microprocessors, application specific integrated circuits (ASICs), memories, sensors, and/or any other suitable hardware configured to execute instructions, code, and/or software. For example, the communication system can include, for example, a sensor or the like configured to sense when the user is speaking to limit and/or reduce the transmission and/or amplification of undesirable background sounds such as sounds associated with heavy or labored breathing, therapy and/or treatment devices (e.g., a nebulizer), and/or adjustment or movement of the mask, hood, etc. Such a sensor can be a pressure sensor or differential pressure (delta-p) sensor configured to sense a change in pressure in the mask, hood, and/or body 110 of the device 100. In some implementations, for example, a delta-p sensor can sense a pressure change within a portion of the device 100 and/or mask and, in response to detecting an upward trend in pressure (e.g., an increase in pressure over a given time), can send a signal to the microphone to begin listing and/or otherwise "picking-up" sound. In some implementations, the microphone and/or the communication system can include one or more filters (e.g., a high pass filter, a low pass filter, and/or a combination thereof) configured to filter out sounds that are outside of a desired frequency (e.g., a frequency range associated with human voices), and/or can include any other suitable active or passive noise cancelling scheme, device, algorithm, etc. The filters can be, for example, hardware filters, software filters, and/or any suitable combination thereof. In some implementations, the communication system can include a microprocessor, memory, and/or any other suitable hardware configured to execute instructions and/or software associated machine learning, artificial intelligence, training, and/or the like configured to perform voice recognition and/or to otherwise learn and/or predict when a user is speaking.

While the respiration passage 120 is described above as being a bidirectional fluid flow path configured to allow a flow of respiration air and/or breath between the user and the filter F (e.g., via the mask fitting 135, the respiration passage 120, and the filter fitting 130), in some implementation, the respiration passage 120 can provide and/or can receive a substantially unidirectional fluid flow through the respiration passage 120 and out of the device 100 via the filter F. For example, in some implementations, the treatment source TS coupled to the treatment fitting 140 can be configured to provide a substantially continuous and/or constant flow of fluid through the treatment passage 125 and the mask fitting 135. The continuous and/or constant flow of fluid (e.g., $O_2$ enriched air or pure $O_2$) can result in a positive pressure within the treatment passage 125 and a volume within the mask M (e.g., between an inner surface of the mask M and the user's face UF). With the seal 145 of the treatment fitting 140 forming a substantially fluid tight seal around and/or with an output of the treatment source TS, the positive pressure associated with a portion of the inlet fluid or treatment that is not drawn into the respiratory system of the user (e.g., during inhalation) can result in a flow of the inlet fluid or treatment into and/or through the respiration passage 120. Moreover, on exhalation, the exhaled breath flows with and/or otherwise mixes with the excess inlet fluid or treatment disposed in the respiration passage 120. In this manner, a substantially unidirectional flow of fluid passes through the respiration passage 120 and out of the device 100 via the filter F.

While the treatment passage 125 is described above as being a unidirectional fluid flow path configured to allow a flow of fluid from the treatment source TS, through the treatment fitting 140 and treatment passage 125, and out the mask fitting 135, in some implementations, the treatment passage 125 can provide bidirectional fluid flow through at least a portion of the treatment passage 125. For example, in some embodiments, the device 100 optionally can include a positive pressure relief valve (RV) that is in fluidic communication with at least a portion of the treatment passage 125. More particularly, the positive pressure relief valve RV can be disposed between at least a portion of the respiration passage 120 and the treatment passage 125 and can be transitioned (e.g., in response to a positive pressure within the treatment passage 125 exceeding a threshold amount of pressure) from a closed state to an open state to allow selective fluidic communication between the treatment passage 125 and the respiration passage 120. In this manner, exhalation breath that is expelled into the treatment passage 125 can flow through at least a portion of the treatment passage 125 and can increase a pressure therein until the pressure exceeds the threshold pressure. Once the threshold pressure is exceeded, the positive pressure relief valve RV can transition from the closed state to the open state allowing the fluid (e.g., exhaled breath) in the treatment passage 125 to flow into the respiration passage 120, where it can then be expelled through the filter F. Moreover, in such implementations, the treatment fitting 140 and/or the seal 145 disposed therein can substantially seal the opening of the treatment fitting 140 (e.g., as described above), thereby limiting and/or substantially preventing fluid (e.g., exhaled breath) from being expelled out of the device 100 via the treatment fitting 140. Thus, the device 100 can allow for respiratory treatment and/or the delivery of an inlet fluid while filtering respiratory air and/or breath whether the treatment passage 125 is configured for unidirectional flow or at least partial bidirectional flow.

FIGS. 2-8 illustrate a respiratory isolation and treatment device 200 according to an embodiment. The respiratory isolation and treatment device 200 (also referred to herein as "device") can be any suitable shape, size, and/or configuration. In some embodiments, for example, the device 200 can be configured for use in any number of settings and adapted to receive, engage, couple to, and/or otherwise function with one or more devices such as masks, hoods, shields, therapeutic and/or oxygen delivery devices, filters, resuscitators, breathing tubes, and/or the like. In some embodiments, the device 200 (and/or portions or aspects thereof) can be similar to and/or substantially the same as the device 100 (and/or portions or aspects thereof). Accordingly, portions and/or aspects of the device 200 may not be described in further detail herein.

As shown in FIGS. 2-5, the respiratory isolation and treatment device 200 includes a body 210, a filter fitting 230 disposed at a first end of the body 210, a mask fitting 235 disposed at a second end of the body 210, and a treatment fitting 240. The body 210 defines a respiration passage 220 extending through and/or otherwise passing between the first end and the second end of the body 210. More particularly, the respiration passage 220 extends through the body 210 and is in fluidic communication with each of the filter fitting 230 disposed at the first end of the body 210 and the mask fitting 235 (or at least a portion thereof) disposed at the second end of the body 210. The body 210 also defines a treatment passage 225 that extends through at least a portion of the body 210. More particularly, the treatment passage 225 extends through at least a portion of the body 210 and is in fluidic communication with each of the treatment fitting 240 and the mask fitting 235 disposed at the second end of the body 210. The arrangement of the body 210 is such that the respiration passage 220 and the treatment passage 225 provide and/or define separated, isolated, distinct, and/or otherwise independent flow paths through at least a portion of the body 210 (as described in further detail herein).

The body 210 can be any suitable shape, size, and/or configuration, and can be formed from any suitable material such as one or more of the biocompatible materials described above. For example, in the embodiment shown in FIGS. 2-8, the body 210 is substantially cylindrical with its first end and its second end being substantially open. The size and/or shape of the body 210 can be based at least in part on a desired size, shape, diameter, etc. of the respiration passage 220 and/or the treatment passage 225 at least partially extending therethrough. Similarly, the body 210 can be include an inner surface that has a shape, size, surface finish, coating, etc. configured to at least partially control (e.g., facilitate, change, modify, enhance, hinder, resist, etc.) a flow of fluid through at least one of the respiration passage 220 and/or the treatment passage 225 such that the fluid flows with one or more desired characteristics and/or the like, as described above with reference to the body 110.

In this embodiment, the body 210 and/or at least a portion of the inner surface includes and/or forms a flow separator 260 that physically and fluidically separates the respiration passage 220 from the treatment passage 225. Said another way, at least a portion of the flow separator 260 disposed in the inner volume of the body 210 includes and/or forms a wall having a first surface that defines a portion of the respiration passage 220 and a second surface, opposite the first surface, that defines a portion of the treatment passage 225, thereby physically and fluidically separating the respiration passage 220 and the treatment passage 225 (at least within the body).

An end portion 266 of the flow separator 260 is shown extending beyond the second end of the body 210 and through or beyond the mask fitting 235. In some embodiments, the flow separator 260 can extend a sufficient distance to allow at least the end portion 266 of the flow separator 260 to be inserted and/or otherwise disposed in the user's mouth when the mask fitting 235 is connected to the mask and the mask is donned by the user. In other embodiments, the flow separator 260 only extends into the mask slightly such that it is not inserted and/or disposed in the user's mouth during use. The end portion 266 of the flow separator 266 includes a wall or surface that extends downward and/or otherwise restricts an opening through the end portion of the flow restrictor 260. The arrangement of the wall or surface at the end portion 266 of the flow separator 260 can direct a fluid flowing out of the treatment passage 225, through the mask fitting 235, and to or toward the mouth of a user donning a mask coupled to the mask fitting 235, as described in further detail herein.

Figure 4:
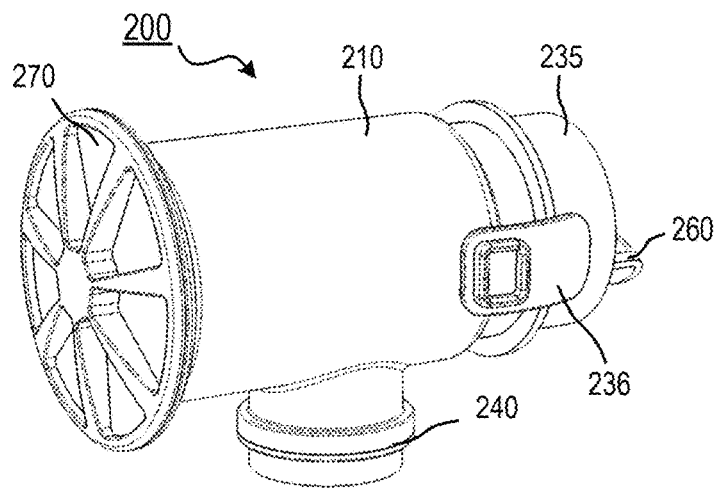

The filter fitting 230 of the device 200 is disposed on or at the first end of the body 210. In the embodiment shown in FIGS. 2-8, the filter fitting 230 is integrally formed with the first end of the body 210 and forms and/or defines an opening that is aligned with and/or otherwise in fluid communication with the respiration passage 220 such that a flow of fluid into or out of the first end of the body 210 passes through the opening. The filter fitting 230 is configured to receive or couple to a filter 270 such as any of those described above with reference to the filter F. In some embodiments, the filter 270 can be fixedly attached to the filter fitting 230. For example, a portion of the filter 270 (e.g., a cap, cover, wall, surface, etc.) can be fixedly secured to the filter fitting 230 via ultrasonic welding, adhesive, and/or any other suitable connection. In other embodiments, the filter 270 can be removably coupled to the filter fitting 230, as described above with reference to the device 100. As shown in FIGS. 4 and 5, the filter 270 is coupled to the filter fitting 230 such that the filter 270 is aligned with, obstructs, and/or otherwise covers the opening defined by the filter fitting 230 and forms a substantially fluid-tight seal with a portion or surface of the filter fitting 230 such that substantially all fluid flow through the first end of the body 210 flows through the opening of the filter fitting 230 and the filter 270 covering the opening. With the respiration passage 220 in fluid communication with each of the filter fitting 230 and the mask fitting 235, respiration air (e.g., inhalation air and exhaled breath) to and/or from the user using the device 200 passes through the respiration passage 220 of the device 200 and the filter 270 coupled to the filter fitting 230, as described in further detail herein.

The mask fitting 235 of the device 200 is disposed on or at the second end of the body 210. In this embodiment, the mask fitting 235 is integrally formed with the second end of the body 210 and forms and/or defines an opening that is aligned with and/or otherwise in fluid communication with the respiration passage 220 and the treatment passage 225 such that a flow of fluid into or out of the second end of the body 210 passes through at least a portion of the opening. For example, the mask fitting 235 can define a first opening in fluid communication with the respiration passage 220 and a second opening in fluid communication with the treatment passage 225. Said another way, the respiration passage 220 can extend through a first portion of the mask fitting 235 and the treatment passage 225 can extend through a second portion of the mask fitting 235 that is different from the first portion of the mask fitting 235.

Although not shown in FIGS. 2-8, the mask fitting 235 is configured to be removably coupled to a mask, hood, shield, and/or the like (collectively referred to as "mask" for simplicity). In some embodiments, the mask fitting 235 can be and/or can form a port that can be removably coupled to a corresponding port on some known masks or to a specifically designed port or coupling portion of any suitable or specifically designed mask, as described above with reference to the mask fitting 135. For example, the mask fitting 235 is shown with attachment mechanisms 236 that can temporarily engage a portion of a mask to at least temporarily couple the mask fitting 235 to the mask. The attachment mechanisms 236 can be, for example, tabs, latches, arms, levers, snaps, threads, etc. In some implementations, a portion of the mask fitting 235 can be inserted into a port, fitting, opening, etc. of a mask and the attachment mechanisms 236 can engage a surface of the mask to collective couple the body 210 to the mask.

The treatment fitting 240 of the device 200 is disposed on or along a portion or side of the body 210 between the first end and the second end. In this embodiment, the treatment fitting 240 is integrally formed with the body 210 and forms and/or defines an opening that is in fluid communication with the treatment passage 225. The treatment fitting 240 is arranged and/or otherwise extends in a substantially perpendicular orientation relative to at least one of the filter fitting 230 and/or the mask fitting 235. For example, a first axis can extend through each of the filter fitting 230 and the mask fitting 235 and a second axis perpendicular or orthogonal to the first axis can extend through the treatment fitting 240. In other embodiments, the treatment fitting 240 can be disposed at any suitable orientation relative to the filter fitting 230 and/or mask fitting 235, as described above with reference to the treatment fitting 140.

The treatment fitting 240 is configured to be removably coupled to an inlet gas source and/or treatment source 280 (referred to herein as "treatment source"). In some embodiments, the treatment fitting 240 can receive at least a portion or output 282 of the treatment source 280 to at least temporarily couple the treatment source 280 to the body 210 of the device 200 (see e.g., FIG. 6). In some embodiments, the treatment fitting 240 and at least a portion of the treatment source 280 can collectively form a friction fit, an interference fit, a press fit, a snap fit, a threaded coupling, and/or any other suitable coupling, as described above with reference to the treatment fitting 140. The treatment fitting 240 can be used with and/or at least temporarily coupled to any suitable treatment source 280 such as, for example, a device configured to deliver a gaseous or aerosolized treatment, therapeutic, medicament, and/or the like (e.g., a nebulizer); an outlet of a reservoir, tank, canister, etc. containing a pressurized fluid such as air, oxygen ($O_2$), nitric oxide (NO), nitrous oxide ($N_2O$) or other anesthetic gases, and/or any other suitable fluid (e.g., gas) or combination of fluids such as oxygen enriched air; a manual resuscitation device; and/or any other suitable device, as described above with reference to the treatment source TS shown in FIG. 1.

The treatment fitting 240 includes a seal 245 configured to selectively engage the treatment source 280 when coupled to the treatment fitting 240. The seal 245, for example, is disposed within the treatment fitting 240 between the treatment passage 225 and an outer opening of the treatment fitting 240. The seal 245 can be any suitable seal, valve, port, etc. In some embodiments, the seal 245 can include multiple seals or portions configured to selectively engage a portion of the treatment source 280 when coupled to the treatment fitting 240. For example, the seal 245 can include a first seal or portion configured to contact an outer surface of the output 282 of the treatment source 280 to form a substantially fluid tight seal therebetween when the treatment source 280 is at least partially inserted into the treatment fitting 240. The seal 245 can also include a seal, valve, or portion configured to transition between a closed state or configuration and an open state or configuration. In the closed state, the seal 245 creates substantial fluidic isolation through the treatment fitting 240 between the treatment passage 225 and a volume outside of the body 210 of the device 200. Conversely, in the open state, the seal 245 can establish fluid communication through treatment fitting 240 allowing the treatment passage 225 to be placed in fluid communication with, for example, the treatment source 280 coupled to the treatment fitting 240.

FIGS. 6 and 7 show a process of coupling the output 282 of the treatment source 280 (e.g., an output of a nebulizer) to the treatment fitting 240. As the output 282 is inserted into the treatment fitting 240, a portion of the seal 245 can engage an outer portion of the output 282 to form a substantially fluid-tight seal therebetween (FIG. 6). As the output 282 is further inserted into the treatment fitting 240, a surface of the output can physically contact a portion of the seal 245, which in turn, can transition that portion from the closed state (e.g., a first configuration) to the open state (e.g., a second configuration). Similarly stated, the output 282 of the treatment source 280 can push one or more portions, valves, flaps, leaflets, etc. to an open position or state. As such, inserting the output 282 of the treatment source 280 into the treatment fitting 240 is operable to establish fluid communication between the treatment source 280 and the treatment passage 225. In some implementations, the seal 245 can be and/or can include a one-way valve that allows a flow of fluid through the valve in a single direction. For example, the seal 245 can be configured to allow a flow of fluid from the treatment source 280 coupled to the treatment fitting 240, into and through the treatment passage 225, and out a portion of the mask fitting 235 at or on the second end of the body 210. Conversely, the seal 245 can be configured to prevent a flow of fluid from the treatment passage 225, into and/or through the treatment fitting 240, and through or past the seal 245 (e.g., out into the environment surrounding the device).

In use, the device 200 can provide and/or deliver a respiratory treatment, therapy, etc. to a user while simultaneously filtering the exchange of respiratory air between the user and the environment outside of the device 200, thereby reducing a potential risk of exposing the user and/or others to undesirable aerosols such as infectious viral or bacterial particles, as well as certain chemicals and/or radionuclides, toxins, and/or the like (e.g., suitable for chemical, biological, radiological, and nuclear defense response). Specifically, in use, the mask fitting 235 can be coupled to the mask (e.g., any suitable mask, hood, shield, etc.) and the filter 270 can be coupled to the filter fitting 230 (e.g., coupled during manufacturing or coupled by a user or medical professional). The mask, hood, shield, and/or the like can be donned by a user such that it covers at least a portion of the user's face (e.g., at least the user's mouth and nose. When coupled to the mask, the mask fitting 235 can be at least partially aligned with the user's mouth and/or the user's nose when the mask is donned by the user. As such, with a portion of the mask fitting 235 in fluid communication with each of the respiration passage 220 and the treatment passage 225, fluid (e.g., respiratory air, room air, oxygen-enriched air, pure oxygen, a therapeutic, a medicament, and/or any other gaseous or aerosolized fluid) can pass between the user's respiratory system and a volume outside of the mask via the mask fitting 235 and at least one of the respiration passage 220 and filter fitting 230 fluidically coupled thereto and/or the treatment passage 225 and the treatment fitting 240 fluidically coupled thereto.

More particularly, the mask fitting 235, the respiration passage 220, and the filter fitting 230 of the device 200 provide a dedicated, bidirectional flow path between the user and the filter 270 coupled to and/or included in the filter fitting 230, which allows for the exchange of filtered inhalation air and/or filtered exhaled breath between the user and the environment outside of the device 200. As such, the filter 270 can filter inhalation air drawn into the device 200, which can protect the user from contaminants in the environmental air, and can filter the exhaled breath expelled by the user out of the device 200, which protects others from contaminants in the exhaled breath (e.g., bacterial and/or viral aerosols carried by the exhaled breath and/or any other undesirable particles carried by the exhaled breath).

In a substantially simultaneous and/or parallel process, the treatment passage 225 provides an independent, separated, isolated, and/or dedicated flow path between the treatment source 280 coupled to the treatment fitting 240 and the user donning the mask, allowing for the delivery of a respiratory treatment, therapy, etc. The flow path through the treatment passage 225 between the treatment fitting 240 and the mask fitting 235 (or portion or opening thereof) is a unidirectional flow path in a direction to and/or toward the user, allowing flow from the treatment source 280 coupled to the treatment fitting 240 to and/or toward the user. For example, the treatment source 280 can be coupled to the treatment fitting 240 (as described above) prior to or after the user dons the mask. The coupling of the treatment source 280 transitions the seal 245 from the closed state to the open state, thereby establishing fluid communication between the treatment source 280 and the treatment passage 225. In this manner, the treatment fitting 240, the seal 245, the treatment passage 225, and the flow separator 260 provide and/or define a substantially unidirectional flow path between the treatment source 280 and the user.

As described above, the end portion 266 of the flow separator 260 extends beyond the mask fitting (e.g., into a volume of the mask, hood, shield, etc. and/or at least partially into the user's mouth) and includes the wall or surface that extends in a downward. As such, the flow of fluid (e.g., a therapeutic and/or the like) from the treatment source 280 flows through the treatment passage 225 and at least a portion of the flow separator 260 and, for example, is directed downward to reduce an amount of mixing with the respiration air being drawn or expelled via the respiration passage 220 (e.g., mixing within a volume defined by the mask).

The wall or surface of at the end portion 266 of the flow separator 260 also limits, reduces, and/or substantially prevents a flow of exhaled breath from flowing into the flow separator 260 and/or the treatment passage 225. In this manner, the body 210 of the device 200, the seal 245, and the treatment source 280 coupled to the treatment fitting 240 can prevent a flow of fluid (e.g., exhaled breath) that may be carrying aerosolized infectious particles from exiting the device 200 through a portion other than the filter fitting 230 and the filter 270 coupled thereto, as described above. As such, the device 200 can be used to deliver respiratory treatment, therapy, etc. to a user who may, for example, have an infectious or contagious condition or disease (e.g., the coronavirus leading to the COVID-19 disease and/or any other infectious or contagious condition or disease) while reducing, limiting, and/or mitigating a risk of spreading the condition or disease, for example, via aerosolized particles carried by the user's exhaled breath.

While the treatment source 280 is shown in FIGS. 6 and 7 as having a particular shape and/or configuration and is described above as being, for example, a nebulizer, it should be understood that the treatment fitting 240 can be coupled to any suitable device. For example, FIG. 8 shows the treatment fitting 240 being coupled to an outlet 286 of a hose, line, tube, etc. connected to a supply of a compressed gas or aerosolized fluid. As a specific example, the outlet 286 can be an outlet of a compressed gas storage/delivery system configured to deliver air, oxygen enriched air having a desired $FiO_2$, pure oxygen, and/or any other suitable gas via the outlet 286. In some implementations, the outlet 286 can be inserted, pressed, threaded, and/or otherwise coupled to the treatment fitting 240 in manner similar to the output 282 shown in FIGS. 6 and 7, and/or in any other suitable manner. Moreover, when the outlet 286 is coupled to the treatment fitting 240, the seal 245 can be transitioned to the open state, as shown in FIG. 8. Thus, the device 200 can be used with any suitable treatment source such as any of those described herein.

FIGS. 9-17 illustrate a respiratory isolation and treatment device 300 according to an embodiment. The respiratory isolation and treatment device 300 (also referred to herein as "device") can be any suitable shape, size, and/or configuration. In some embodiments, for example, the device 300 can be configured for use in any number of settings and adapted to receive, engage, couple to, and/or otherwise function with one or more devices such as masks, hoods, shields, therapeutic and/or oxygen delivery devices, filters, resuscitators, and/or the like. In some embodiments, the device 300 (and/or portions or aspects thereof) can be similar to and/or substantially the same as the devices 100 and/or 200 (and/or portions or aspects thereof). Accordingly, portions and/or aspects of the device 300 may not be described in further detail herein.

Figure 9:
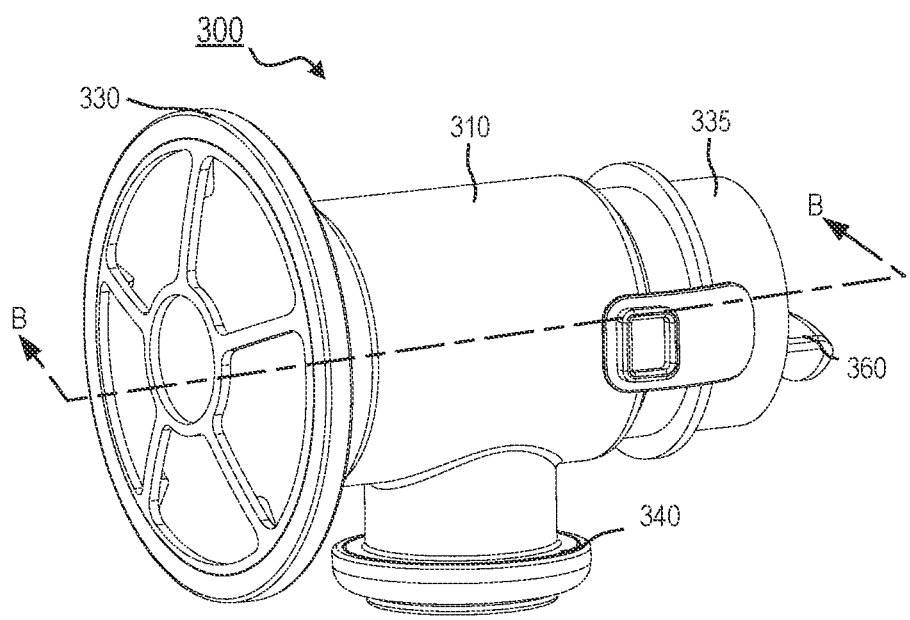
FIGS. 9 and 10 are a front-side perspective view and a rear-side perspective view of a respiratory isolation and treatment device according to an embodiment.
Figure 10:
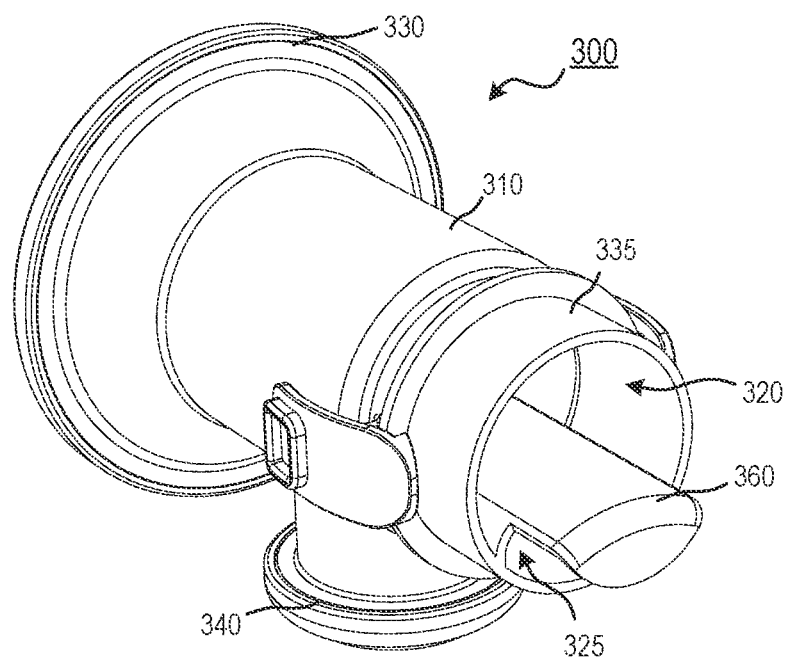

As shown in FIGS. 9-11, the device 300 includes a body 310, a filter fitting 330 disposed at a first end of the body 310, a mask fitting 335 disposed at a second end of the body 310, and a treatment fitting 340. The body 310 defines a respiration passage 320 extending through and/or otherwise passing between the first end and the second end of the body 310. More particularly, the respiration passage 320 extends through the body 310 and is in fluidic communication with each of the filter fitting 330 disposed at the first end of the body 310 and the mask fitting 335 (or at least a portion thereof) disposed at the second end of the body 310. The body 310 also defines a treatment passage 325 that extends through at least a portion of the body 310. More particularly, the treatment passage 325 extends through at least a portion of the body 310 and is in fluidic communication with each of the treatment fitting 340 and the mask fitting 335 disposed at the second end of the body 310. The arrangement of the body 310 is such that the respiration passage 320 and the treatment passage 325 provide and/or define separated, isolated, distinct, and/or otherwise independent flow paths through at least a portion of the body 310, as described in detail above with reference to the devices 100 and/or 200.

The body 310 can be any suitable shape, size, and/or configuration, and can be formed from any suitable material such as one or more of the biocompatible materials described above. The body 310 includes and/or forms a flow separator 360 at least partially disposed an inner volume of the body 310. The body 310 can be similar to and/or substantially the same in form and/or function as the body 210 described above with reference to FIGS. 2-8. Similarly, the filter fitting 330 and the mask fitting 335 can be substantially similar to the filter fitting 230 and the mask fitting 235, respectively, described above with reference to FIGS. 2-8.

For example, the filter fitting 330 is disposed or formed on or at the first end of the body 310 and is in fluid communication with the respiration passage. The filter fitting 330 is configured to receive or couple to a filter 370 such as any of those described above with reference to the filters 170 and/or 270. The mask fitting 335 is disposed and/or formed on or at the second end of the body 310 and is aligned with and/or otherwise in fluid communication with each of the respiration passage 320 and the treatment passage 325 such that a flow of fluid into or out of the second end of the body 310 passes through the mask fitting 335. Although not shown, the mask fitting 335 is configured to be removably coupled to a mask, hood, shield, and/or the like (collectively referred to as "mask" for simplicity), as described in detail above with reference to the mask fittings 135 and/or 235.

The device 300 can differ from the device 200, however, in the arrangement and/or form of the treatment fitting 340. In this embodiment, the treatment fitting 340 is disposed or formed on or along a portion or side of the body 310 between the first end and the second end and includes a seal 345 disposed within an opening that is in fluid communication with the treatment passage 325. The treatment fitting 340 is configured to be at least temporarily coupled to a treatment source 380 (referred to herein as "treatment source"), as described above with reference to the treatment fittings 140 and/or 240. The treatment fitting 340 can be used with and/or at least temporarily coupled to any suitable treatment source 380 such as any of those described above.

As shown in FIGS. 11-14, the seal 345 includes a seal portion 346 and a valve portion 347. The seal portion 346 includes one or more ribs, O-rings, seals, and/or the like configured to selectively engage and/or contact a portion of the treatment source 380 to form a substantially fluid tight seal therebetween when the treatment source 380 is at least partially disposed in and/or coupled to the treatment fitting 340. The valve portion 347 can include any number of leaflets, arms, flaps, etc. and can be configured to transition between a closed state and an open state. In some embodiments, for example, the valve portion 347 can include and/or can form a duckbill valve and/or any other suitable one-way valve. Each leaflet, arm, flap, etc. of the valve portion 347 can include and/or can form a rib 348 that can be contacted to transition the valve portion 347 between the closed state and the open state.

Figure 14:
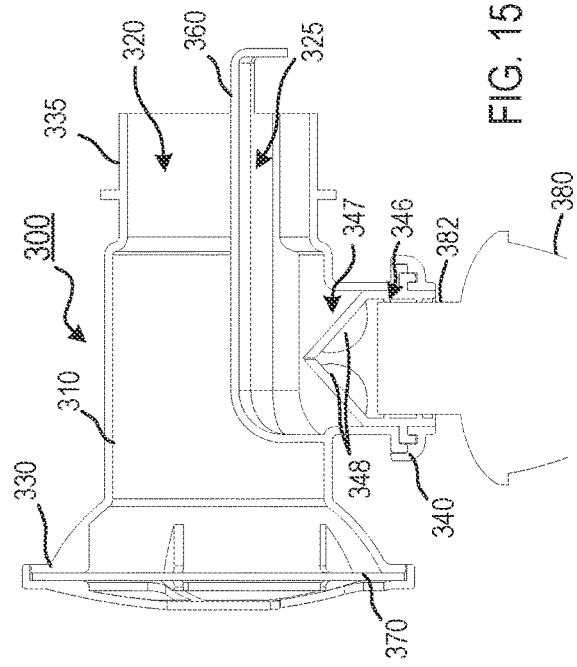
FIGS. 14-17 are cross-sectional views of the device of FIG. 9 taken along the line B-B and illustrating a process of coupling the treatment fitting to a treatment source according to an embodiment.
Figure 15:
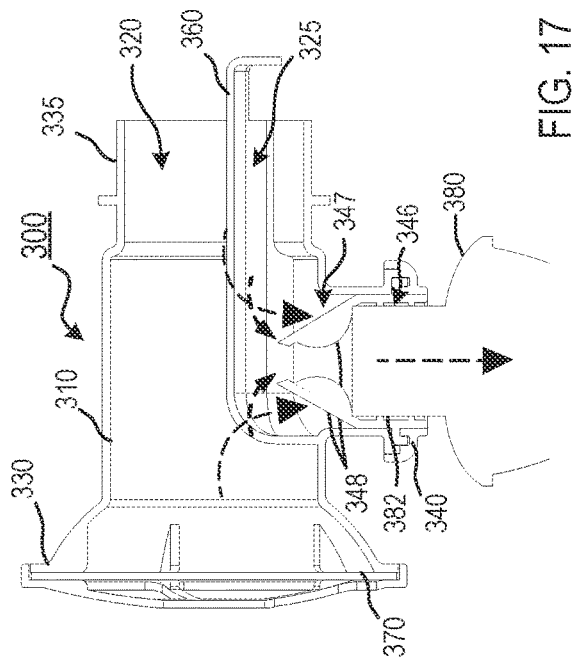

For example, FIG. 14 shows the seal 345 and/or the valve portion 347 thereof in a closed state (e.g., prior to the treatment source 380 being coupled to the treatment fitting 340). In the closed state, the seal 345 and/or the valve portion 347 thereof creates substantial fluidic isolation through the treatment fitting 340 between the treatment passage 325 and a volume outside of the body 310 of the device 300. That is to say, when the seal 345 is in the closed state, the seal 345 substantially prevents a flow of fluid trough the treatment fitting 340 and into the treatment passage 325, as well as a flow of fluid through the treatment passage 325 and out the treatment fitting 340. FIG. 15 shows an output 382 of the treatment source 380 partially inserted into the treatment fitting 340. The seal portion 346 of the seal 345 is shown engaging an outer surface of the outlet 382, which can form a substantially fluid-tight seal therebetween, thereby substantially preventing a flow of fluid outside of the device 300 and/or the treatment source 380 from flowing through the treatment fitting 340. In this manner, the treatment fitting 340 and/or the seal 345 allow a unidirectional flow of fluid through the treatment fitting 340 (e.g., supplied by the treatment source 380 coupled thereto) and into the treatment passage 325.

Figure 16:
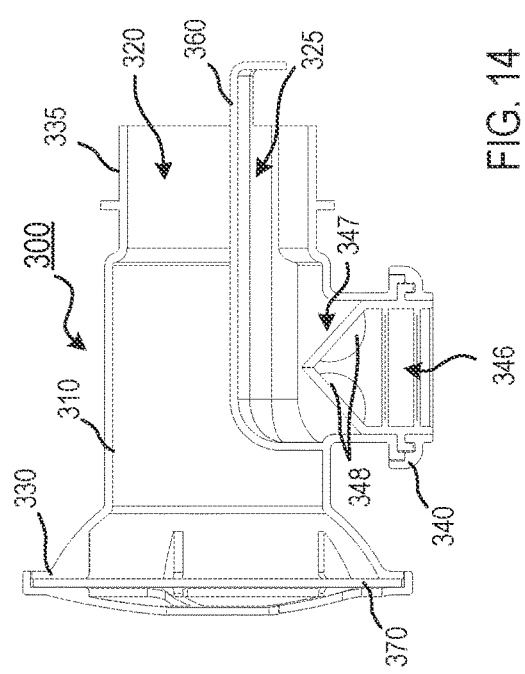
Figure 17:
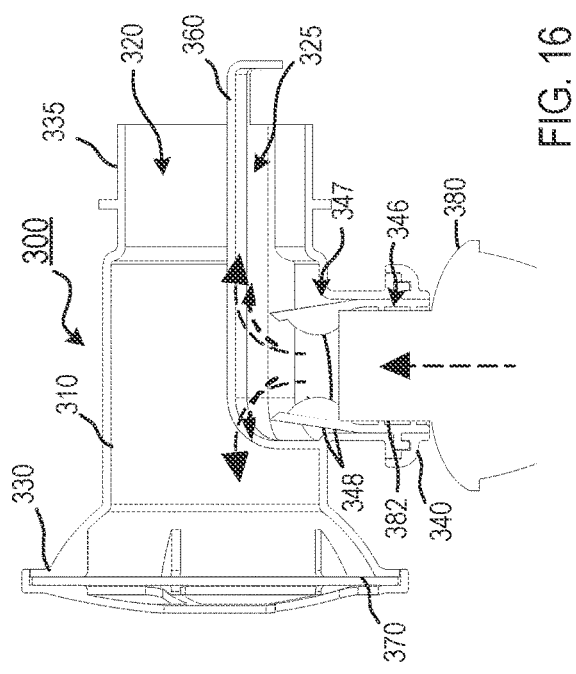

FIG. 16 shows the treatment source 380 fully coupled to and/or inserted in the treatment fitting 340. The valve portion 347 is shown as having been transitioned from the closed state (FIGS. 14 and 15) to the open state. More specifically, the output 382 of the treatment source 380 can be inserted into the treatment fitting 340 a sufficient amount that a surface of the output 382 of the treatment source 380 contacts the ribs 348 of the valve portion 347, resulting in a force operable to transition the valve portion 347 from the closed state to the open state. With the seal 345 and/or valve portion 347 in the open state, a fluid can flow from the treatment source 380, through the treatment passage 325, and into the respiratory system of a user. FIG. 17 shows the treatment source 380 being withdrawn from the treatment fitting 340 (e.g., after delivering a therapeutic treatment and/or the like). As the treatment source 380 is withdrawn, the valve portion 347 is shown transitioning from the open state back to the closed state. As such, when the treatment source 380 is withdrawn an amount sufficient to remove the output 382 from contact with the ribs 348 of the valve portion 347, the seal 345 and/or valve portion 347 thereof will be in the closed state.

As described above, any of the respiratory treatment devices can be configured to removably receive and/or couple to a filter. In some implementations, the removable arrangement of the filter relative to the filter fitting can allow a filter to be replaced during use, while ensuring that respiratory air flowing into or out of the filter fitting is filtered. For example, FIGS. 18-23 illustrate a respiratory isolation and treatment device 400 according to an embodiment. The respiratory isolation and treatment device 400 (also referred to herein as "device") can be any suitable shape, size, and/or configuration. In some embodiments, for example, the device 400 can be configured for use in any number of settings and adapted to receive, engage, couple to, and/or otherwise function with one or more devices such as masks, hoods, shields, therapeutic and/or oxygen delivery devices, filters, resuscitators, and/or the like. In some embodiments, the device 400 (and/or portions or aspects thereof) can be similar to and/or substantially the same as the devices 100, 200, and/or 300 (and/or portions or aspects thereof). Accordingly, portions and/or aspects of the device 400 may not be described in further detail herein.

Figure 18:
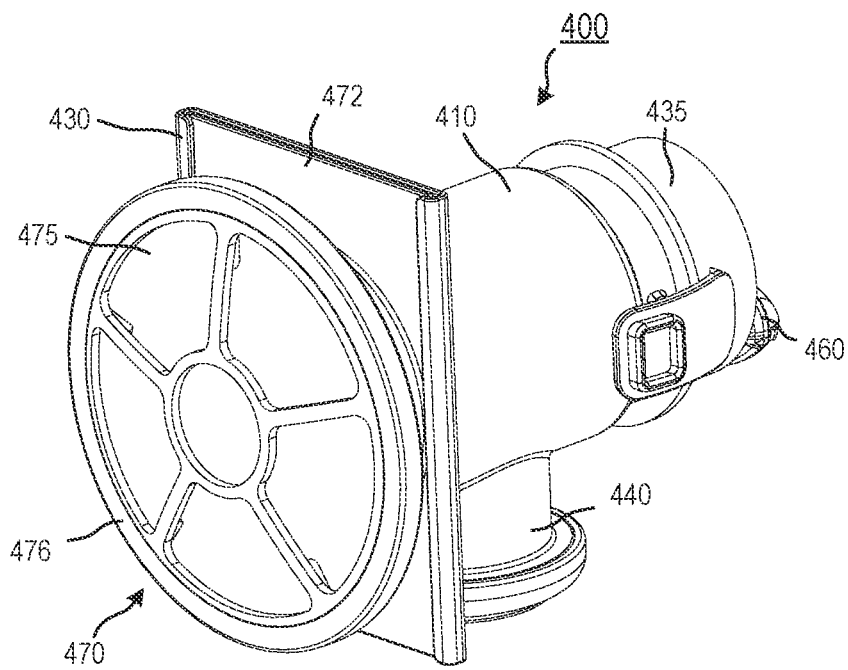
FIG. 18 is a perspective view of a respiratory isolation and treatment device according to an embodiment and shown with a filter being removably coupled to a filter fitting of the device.
Figure 19:
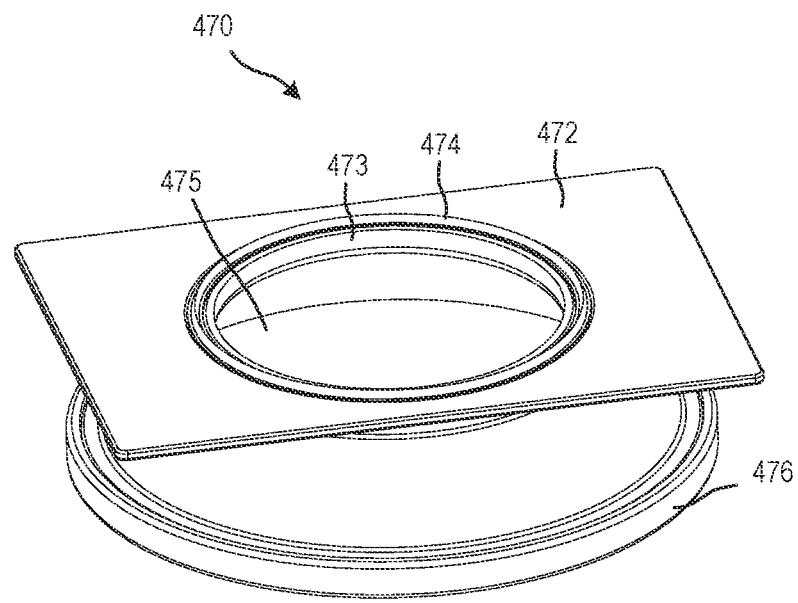
FIG. 19 is a back-perspective view of the filter shown in FIG. 18.

As shown in FIGS. 18 and 19, the device 400 includes a body 410, a filter fitting 430 disposed at a first end of the body 410, a mask fitting 435 disposed at a second end of the body 410, and a treatment fitting 440. The body 410 defines a respiration passage (not shown in FIGS. 18-23) extending through and/or otherwise passing between the first end and the second end of the body 410. More particularly, the respiration passage extends through the body 410 and is in fluidic communication with each of the filter fitting 430 disposed at the first end of the body 410 and the mask fitting 435 (or at least a portion thereof) disposed at the second end of the body 410. The body 410 also defines a treatment passage (not shown in FIGS. 18-23) that extends through at least a portion of the body 410 and is in fluidic communication with each of the treatment fitting 440 and the mask fitting 435 disposed at the second end of the body 410. The arrangement of the body 410 is such that the respiration passage and the treatment passage provide and/or define separated, isolated, distinct, and/or otherwise independent flow paths through at least a portion of the body 410, as described in detail above with reference to the devices 100, 200, and/or 300.

The body 410 can be any suitable shape, size, and/or configuration, and can be formed from any suitable material such as one or more of the biocompatible materials described above. The body 410 includes and/or forms a flow separator 460 at least partially disposed an inner volume of the body 410. The body 410 can be similar to and/or substantially the same as the body 210 described above with reference to FIGS. 2-8. Similarly, the mask fitting 435 and the treatment fitting 440 can be substantially similar to the mask fitting 235 and the treatment fitting 240 and/or 340, respectively, described in detail above. Accordingly, the body 410, the mask fitting 435, and the treatment fitting 440 are not described in further detail herein.

The device 400 can differ from the devices 200 and/or 300, however, in the arrangement and/or form of the filter fitting 430. The filter fitting 430 is disposed or formed on by the first end of the body 410 and defines an opening that is in fluid communication with the respiration passage. In this embodiment, the filter fitting 430 is configured to be at least temporarily and/or removably coupled to a filter 470 or filter assembly, as described above with reference to the filter fitting 130.

The filter fitting 430 can be used with and/or at least temporarily coupled to any suitable filter 470 such as any of those described above. As shown in FIGS. 18 and 19, for example, the filter 470 (or filter assembly) can include a backplate 472, a seal 474, a filter material 475, and a faceplate 476. FIG. 18 shows the filter material 475 being disposed between the backplate 472 and the faceplate 476. The faceplate 476 is shown covering and/or at least partially enclosing the filter material 475 and having a substantially open configuration, for example, to allow air to flow through the filter material 475. While the faceplate 476 is shown in FIG. 18 as having a particular configuration, it should be understood that the faceplate 476 can have any suitable shape and/or configuration that allows for a desired amount of air flow through the filter material 475.

The backplate 472 can be a substantially flat plate or surface configured to couple the filter 470 to the filter fitting 430. For example, the filter fitting 430 can include and/or form a substantially flat plate with rails or tracks along the sides of the filter fitting 430 to allow at least a portion of the backplate 472 of the filter 470 to be inserted and/or slid into a desired position relative to the filter fitting 430 (and/or an opening defined by the filter fitting 430, not shown in FIGS. 18-23). The rails, tracks, and/or edges of the filter fitting 430 can be configured to expand in response to the filter 470 being coupled to the filter fitting 430, which in turn, can result in the rails, tracks, and/or edges exerting a clamping force along the edges or sides of the backplate 476, thereby at least temporarily retaining the filter 470 in a fixed position relative to the filter fitting 430.

FIG. 19 is a back view of the filter 470 showing the backplate 472. The backplate 472 defines an opening 473 and includes and/or is coupled to the seal 474, which encircles, circumscribes, and/or surrounds the opening 473. The seal 474 can be any suitable seal such as, for example, an O-ring, a gasket, and/or the like. Although not shown in FIG. 18, the filter 470 can be removably coupled to the filter fitting 430 and positioned such that the opening 473 defined by the backplate 472 is substantially aligned with the opening defined by the filter fitting 430. In addition, the seal 474 can engage and/or contact a surface of the filter fitting 430 to form a substantially fluid-tight seal around the openings. Thus, when the filter 470 (or filter assembly) is coupled to the filter fitting 430, substantially all fluid flow through the first end of the body 410 flows through the opening of the filter fitting 430 and the filter material 475 of the filter 470 removably coupled thereto. With the respiration passage in fluid communication with each of the filter fitting 430 and the mask fitting 435, respiration air (e.g., inhalation air and exhaled breath) to and/or from the user using the device 400 passes through the filter material 475 thereby protecting the user and/or other people from undesirable particles such as aerosols carried by the user's exhaled breath and/or the like, as described in detail above with reference to the devices 100, 200, and/or 300.

Figure 20:
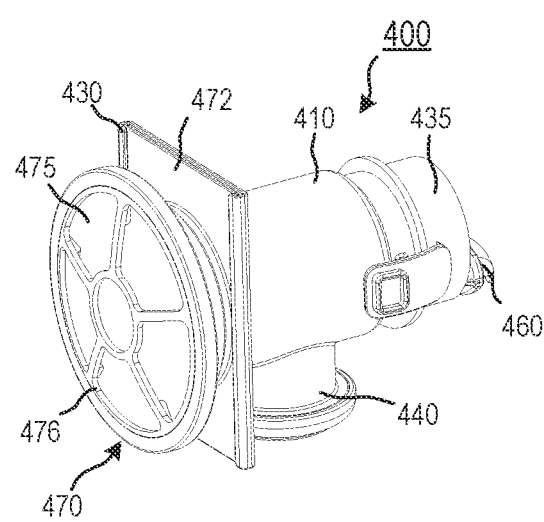
FIGS. 20-23 are perspective views of the device of FIG. 18 and illustrating a process of replacing filters removably coupled to a filter fitting of the device.
Figure 21:
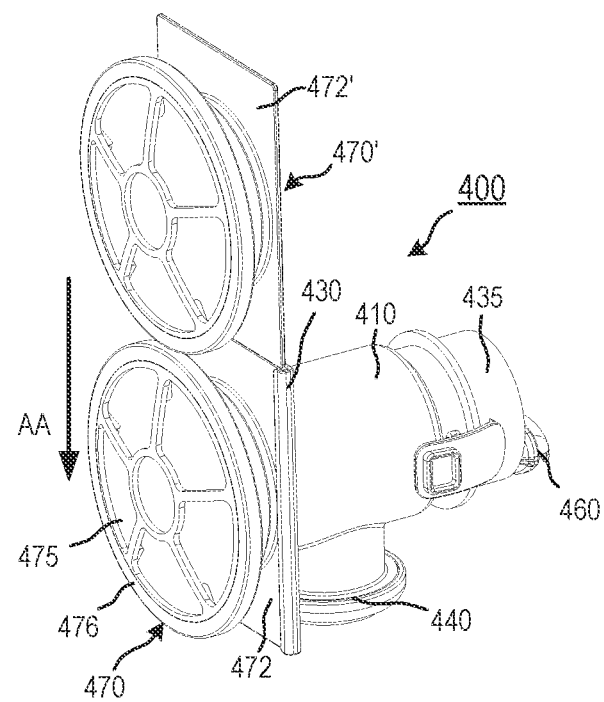

FIGS. 20-23 illustrate a process of replacing the filter 470 removably coupled to the filter fitting 430 with a replacement filter 470'. FIG. 20 shows the filter 470 removably coupled to the filter fitting 430 prior to replacement. FIG. 21 shows an initiation of a filter replacement process. For example, in some instances, when the original filter 470 is coupled to the filter fitting 430, the replacement filter 470' can be positioned such that a baseplate 472' of the replacement filter 470' is adjacent a free surface of the baseplate 472 of the original filter 470 and substantially aligned and/or parallel with, for example, with the rails or tracks formed along the sides of the filter fitting 430. Once aligned, a force can be exerted on the replacement filter 470' in a direction parallel to the rails, tracks, edges, etc. of the filter fitting as indicated by the arrow AA in FIG. 21.

Figure 22:
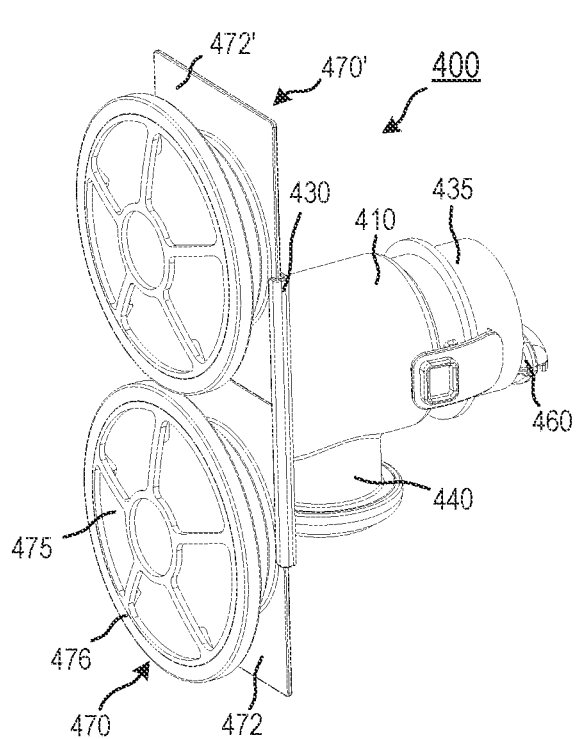
Figure 23:
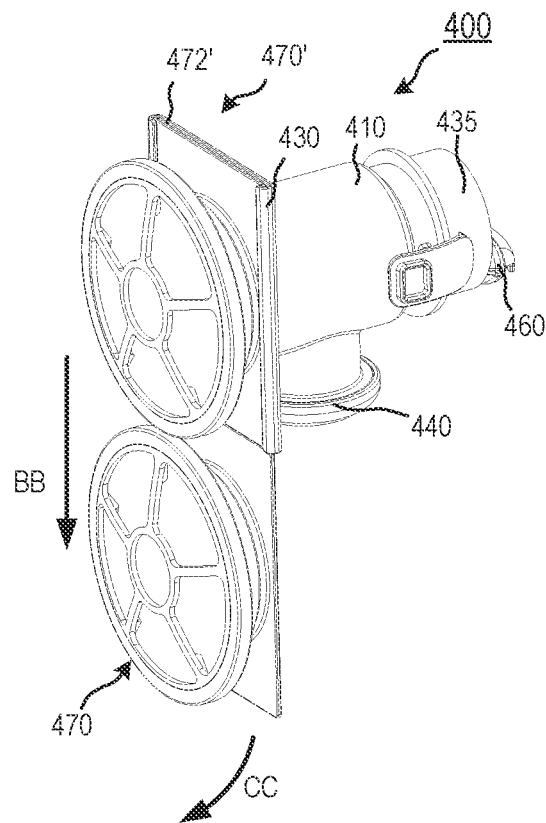

FIG. 22 shows the original filter 470 and the replacement filter 470' in an intermediate position in which a portion of the each of the filters 470 and 470' is coupled to the filter fitting 430. In some implementations, the arrangement of the filter fitting 430, the backplates 472 and 472', and the seals 474 (see FIG. 19) and be such that airflow through the opening defined by the filter fitting 430 and not through at least one of the filters 470 and/or 470' is reduced or substantially prevented. For example, in some implementations, a back surface of the backplates 472 and 472' can be in contact or at least partial contact with an opposite surface of the filter fitting 430 thereby limiting or substantially preventing a flow of fluid therebetween. As indicated by the arrow BB in FIG. 23, the filters 470 and 470' can be moved through the intermediate position (FIG. 22) to a final position in which the replacement filter 470' is in a desired position relative to the filter fitting 430 and the original filter 470 is decoupled from the filter fitting 430 allowing the original filter 470 to be removed from the device 400, as indicated by the arrow CC in FIG. 23. As such, the device 400 can allow for replacement of filters while limiting and/or substantially preventing an unfiltered flow of fluid (e.g., exhaled breath) from being expelled from the device 400.

Although not shown, in some embodiments, the filter 470 and/or the backplate 472 can include a cap, cover, film, seal, and/or the like configured to cover the opening 473 after the filter 470 is removed from the filter fitting 430. In some implementations, the cap, cover, film, seal, and/or the like (collectively referred to as "cover") can be configured to transition automatically upon removal from the filter fitting 430 from a first configuration in which the opening 473 is uncovered to a second configuration in the opening 473 is substantially covered or otherwise blocked. Similarly, in some implementations, the replacement filter 470' can include a cover that substantially covers the opening prior to being coupled to the filter fitting 430 and that is transitioned to an uncovered state as the replacement filter 470' is coupled to the filter fitting 430.

While the filters 470 and 470' are shown being moved in a downward direction (e.g., in the direction of the arrows AA and BB in FIGS. 21 and 23, respectively), it should be understood that the filters 470 and 470' can be moved in any suitable direction during replacement based at least in part on an orientation of the device 400, and/or the configuration of the filter fitting 430. For example, while the rails, tracks, and/or edges of the filter fitting 430 are arranged in a substantially vertical orientation, in some embodiments, the rails, tracks, and/or edges can be arranged in any suitable orientation (e.g., a substantially horizontal orientation and/or any suitable diagonal or non-orthogonal orientation relative to the vertical orientation shown in FIGS. 18-23).

While FIG. 22 shows each of the original filter 470 and the replacement filter 470' in a specific position it should be understood that such positions are presented for illustration purposes only to aid in the description of certain aspects and/or characteristics of the replacement process. The process of replacing a filter 470, for example, need not include placing the original filter 470 and replacement filter 470' in a discreet intermediate position. Similarly stated, the replacement process can include a single continuous movement of the filters 470 and 470' from the initial positions shown in FIG. 21 to the final positions shown in FIG. 23. In other instances, a replacement process can include placing the filters 470 and 470' in any number of intermediate positions.

While the devices 200, 300, and/or 400 have been described above as including a flow separator that is a substantially fixed portion and/or feature of the body of the device, in other embodiments, a treatment device can include and/or form a dynamic flow separator configured to transition between two or more configurations. For example, FIGS. 24-30 illustrate a respiratory isolation and treatment device 500 according to an embodiment. The respiratory isolation and treatment device 500 (also referred to herein as "device") can be any suitable shape, size, and/or configuration. In some embodiments, for example, the device 500 can be configured for use in any number of settings and adapted to receive, engage, couple to, and/or otherwise function with one or more devices such as masks, hoods, shields, therapeutic and/or oxygen delivery devices, filters, resuscitators, and/or the like. In some embodiments, the device 500 (and/or portions or aspects thereof) can be similar to and/or substantially the same as the devices 100, 200, 300, and/or 400 (and/or portions or aspects thereof). Accordingly, portions and/or aspects of the device 500 may not be described in further detail herein.

The device 500 includes a body 510, a filter fitting 530 disposed at a first end of the body 510, a mask fitting 535 disposed at a second end of the body 510, and a treatment fitting 540. The filter fitting 530 can be similar in at least form and/or function to the filter fitting 430 (FIGS. 18-23), the mask fitting 535 can be similar in at least form and/or function to the mask fitting 230 (FIGS. 2-8), and the treatment fitting 540 can be similar in at least form and/or function to the treatment fitting 340 (FIGS. 9-17). Accordingly, filter fitting 530, the mask fitting 535, and the treatment fitting 540 are not described in further detail herein.

At least some portions and/or aspects of the body 510 can be similar in at least form and/or function to corresponding portions and/or aspects of the body 210 (FIGS. 2-8). For example, the body 510 defines a respiration passage 520 in fluidic communication with each of the filter fitting 530 disposed at the first end of the body 510 and the mask fitting 535 (or at least a portion thereof) disposed at the second end of the body 510. The body 510 also defines a treatment passage 525 that is in fluidic communication with each of the treatment fitting 540 and the mask fitting 535 disposed at the second end of the body 510, as described above with reference to the body 210.

Figure 24:
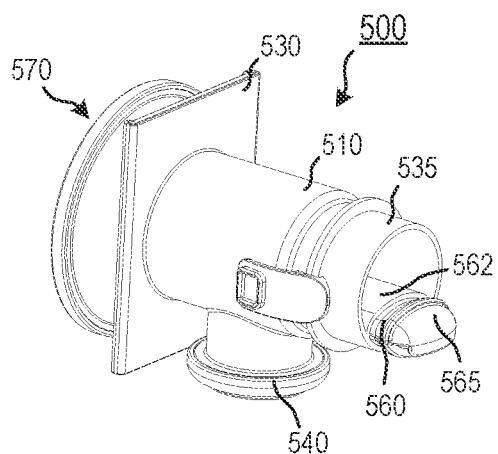
FIGS. 24 and 25 are a side-perspective view and a cross-sectional view, respectively, of a respiratory isolation and treatment device in a first configuration, according to an embodiment.
Figure 25:
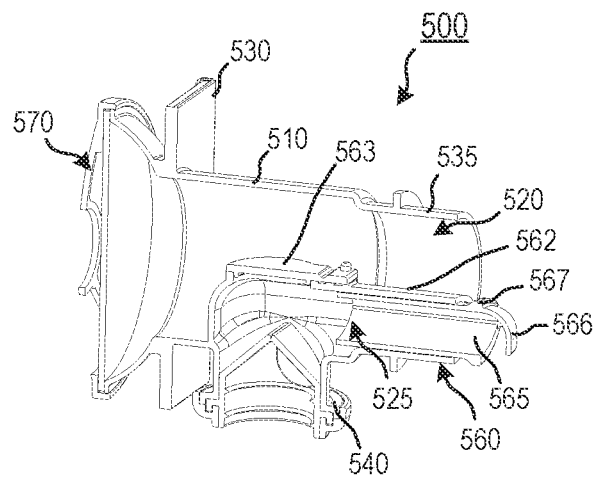

The body 510 can differ from the body 210, however, by including a dynamic flow separator 560 configured to transition between two or more configurations. FIGS. 24 and 25 illustrate the flow separator 560 in a first configuration. The flow separator 560 is shown as including a first portion 562 and a second portion 565 at least partially disposed in the first portion 562. The first portion 562 of the flow separator 560 can be, for example, integrally formed with the body 510 and disposed within an inner volume of the body 510. The first portion 562 of the flow separator 560 at least partially separates the respiration passage 520 from the treatment passage 525 within the body 510. Said another way, the first portion 562 of the flow separator 560 is disposed in the inner volume of the body 510 includes and/or forms a wall having a first surface that defines a portion of the respiration passage 520 and a second surface, opposite the first surface, that defines a portion of the treatment passage 525, thereby separating the respiration passage 520 and the treatment passage 525. In this embodiment, the first portion 562 includes a positive pressure relief valve 563 configured to selectively place the treatment passage 525 in fluid communication with the respiration passage 520, as described in further detail herein.

Figure 26:
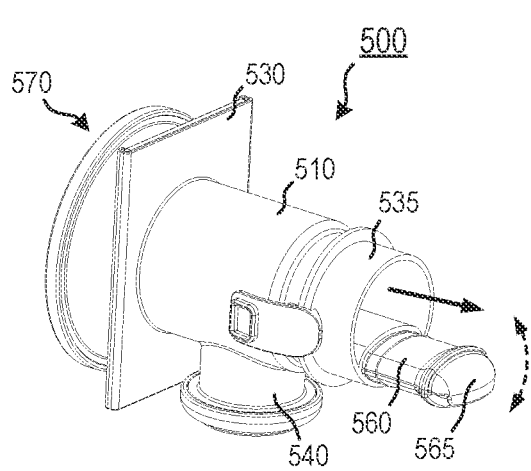
FIGS. 26 and 27 are a side perspective view and a cross-sectional view, respectively, of the device of FIG. 24 shown in a second configuration.
Figure 27:
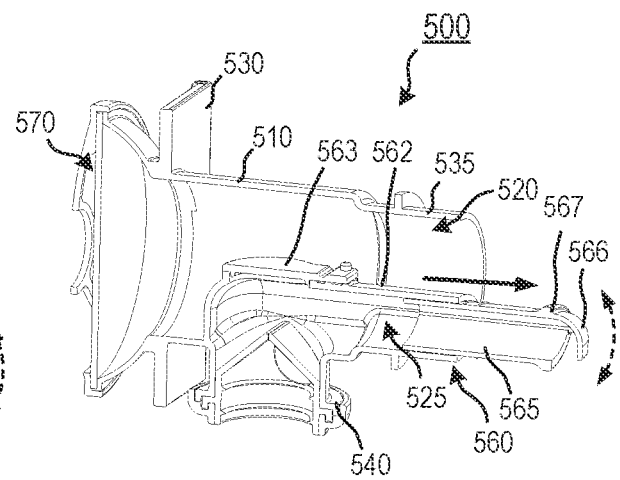

The second portion 565 of the flow separator 560 is movably coupled to the first portion of the flow separator 560. For example, the second portion 565 is at least partially disposed in the first portion 562 and is configured to be moved relative to the first portion to transition the flow separator between a first configuration and a second configuration. In this embodiment, for example, the flow separator 560 can have a telescoping configuration, with the second portion 565 being movably relative to the first portion 562 between a first position and a second position. FIGS. 24 and 25 show the second portion 565 extending a first distance from the first portion 562 of the flow separator 560 when in the first position (e.g., when the flow separator 560 is in the first configuration). FIGS. 26 and 27 show the second portion 565 extending a second distance from the first portion 562 when in the second position (e.g., when the flow separator 560 is in the second configuration). The second distance is greater than the first distance and, in some instances, can be sufficient to all at least an end 566 of the second portion 565 to be inserted and/or otherwise disposed in the user's mouth when the mask fitting 535 is connected to a mask and the mask is donned by the user. The end 566 of the second portion 565 includes a wall or surface that extends downward and/or otherwise restricts an opening through the end 566 of the second portion 565, which can direct a fluid flowing out of the flow separator 560 and to or toward the mouth of a user donning a mask, as described above with reference to the flow separator 260. The end 566 can also include a ridge, protrusion, rib, bump, and/or any other suitable engagement feature configured to facilitate and/or enhance the ergonomics associated with inserting at least the end 566 into a user's mouth.

Figure 28:
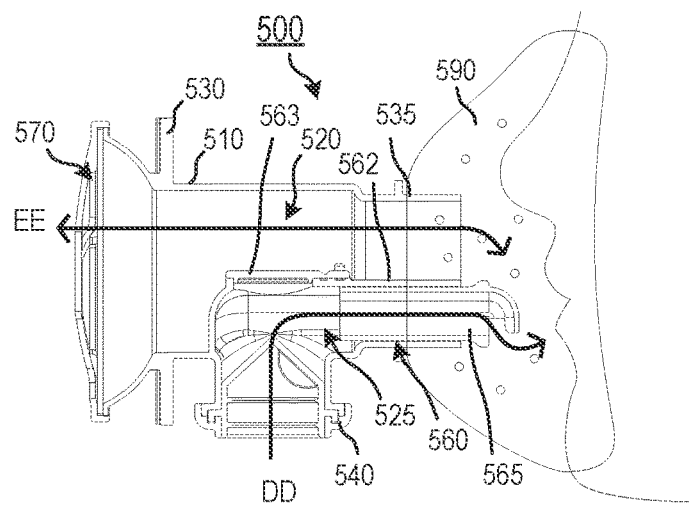
FIGS. 28-30 are cross-sectional views of the respiratory isolation and treatment device of FIG. 24 shown, in use, in the first configuration, the second configuration, and a third configuration, respectively.
Figure 29:
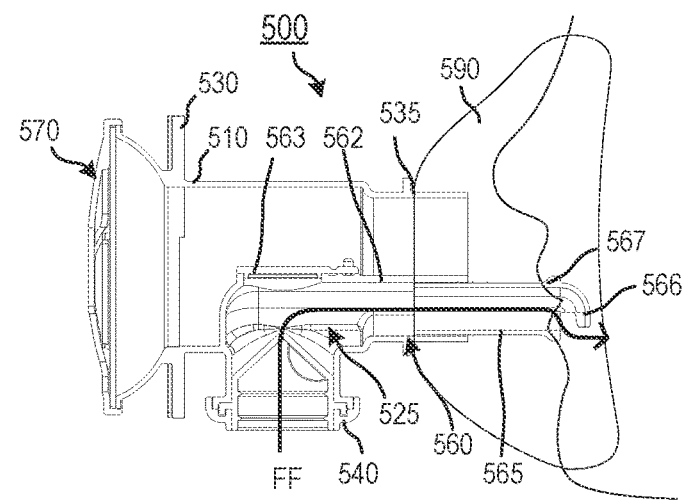
Figure 30:
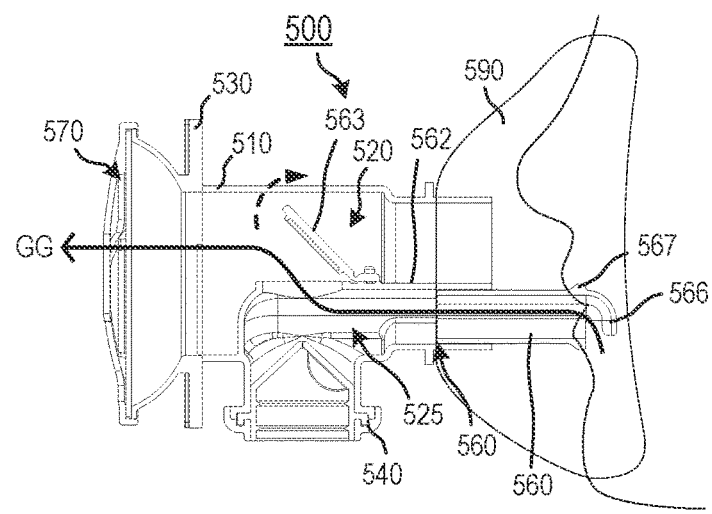

FIGS. 28-30 show the device 500 coupled to a mask 590 donned by a user. FIG. 28 shows the device 500 in a first configuration with the flow separator 560 in a retracted state (e.g., its first configuration). Said another way, the second portion 565 of the flow separator 560 is in the first position relative to the first portion 562. As shown, the second portion 565 extends beyond the mask fitting 535 and into a volume defined by the mask 590 but, in this example, is not disposed in the user's mouth. In addition, the positive pressure relief valve 563 included in the first portion 562 of the flow separator 560 is shown in a closed state such that the respiration passage 520 and the treatment passage 525 are physically and fluidically separated, at least within the body 510 of the device 510. In the first configuration, the device 510 can be at least functionally similar to the device 210 described above with reference to FIGS. 2-8. As such, an inlet gas source and/or treatment source (not shown) can be coupled to the treatment fitting 540 and can deliver, via the treatment passage 525 and the flow separator 560, a flow of a gaseous and/or aerosolized fluid to the user donning the mask 590. More particularly, with the device 500 in the first configuration, the treatment passage 525 and the flow separator 560 provide a unidirectional fluid flow path to and/or toward the user, as indicated by the arrow DD in FIG. 28. In a substantially concurrent and/or parallel process, the respiration passage 520 can provide a bidirectional fluid flow path configured to allow a flow of respiration air (e.g., inhalation air and exhaled breath) between the user and the environment outside the device 500 via the filter 570, as indicated by the arrow EE in FIG. 28.

FIG. 29 shows the device 500 in a second configuration with the flow separator 560 in an extended state (e.g., its second configuration). Said another way, the second portion 565 of the flow separator 560 is in the second position relative to the first portion 562. As shown, the second portion 565 extends beyond the mask fitting 535, through the volume defined by the mask 590, and at least partially into the user's mouth. The user can engage the end 566 and/or the engagement feature 567 to temporarily secure the end 566 of the second portion 565 of the flow separator 560 in the user's mouth. In some instances, placing the device 500 in the second configuration can allow for a targeted and/or direct delivery of a therapeutic treatment via the treatment passage 525. Specifically, the treatment source (e.g., any of those described herein) can be coupled to the treatment fitting 540 can provide a flow of a gaseous and/or aerosolized fluid (e.g., a therapeutic, medicament, air, oxygen, oxygen enriched air, and/or any other suitable fluid), as indicated by the arrow FF in FIG. 29.

FIG. 30 shows the device 500 in a third configuration with the positive pressure relief valve 563 of the flow separator 560 transitioned from the closed state to an open state to at least temporarily establish fluid communication between the treatment passage 525 and the respiration passage 520. For example, the second portion 565 of the flow separator 560 is shown in the second position and is at least partially disposed in the user's mouth. During an inhalation phase of respiratory treatment, the user can create and/or produce a suction force (e.g., a negative pressure differential) operable to draw a flow of the fluid through the treatment passage 525 and flow separator 560 and into the user's respiratory system, as indicated by the arrow FF in FIG. 29. In some implementations, the suction force can also act on the positive pressure relief valve 563 to maintain the positive pressure relief valve 563 in a substantially closed state (FIG. 29). During an exhalation phase of the respiratory treatment, the user can expel a flow of exhaled breath into the flow separator 560 and through the treatment passage 525. The exhalation, for example, can produce a positive pressure differential within at least a portion of the treatment passage 525 operable to transition the positive pressure relief valve 563 from the closed state to the open state, thereby allowing the exhaled breath to flow through the positive pressure relief valve 563, into and through a portion of the respiration passage 570, and out of the filter 570, as indicated by the arrow GG in FIG. 30. In this manner, the device 500 can be used to deliver a respiratory treatment while filtering respiration air between the user and the environment outside of the device 500.

While the second portion 565 of the flow separator 560 is described above being configured to extend (e.g., advance in a linear direction), in some embodiments, a treatment device can include a flow separator configured to transition and/or move with any suitable range of motion and/or degree of freedom. For example, in some embodiments, a flow separator and/or at least a portion thereof can be configured to articulate, bend, bow, rotate, twist, extend, and/or otherwise reconfigure in any suitable manner. In some implementations, the flow separator can be bent, flexed, etc. to allow an end of the flow separator to be disposed comfortably in the user's mouth. For example, at least a region along the second portion 565 of the flow separator 560 can be formed of a relatively soft and/or flexible material, can include a corrugation, living hinge, etc., and/or can have any other suitable configuration allowing for a desired amount of flexibility, bending, and/or reconfiguration (see e.g., the dash-line arrows in FIGS. 26 and 27). In some implementations, including a flow separator, for example, that can extend and bend or flex a desired amount and/or in a desired direction can allow a treatment device to provide a targeted delivery of a therapeutic to a user receiving respiratory treatment.

Although not shown in FIGS. 24-30, the device 500 can include any suitable actuator and/or the like configured to transition the flow separator from the first state to the second state. The actuator can be any suitable shape, size, and/or configuration. For example, in some embodiments, the actuator can be a slider or the like that is coupled to the second portion 565 of the flow separator 560 and extends, at least in part, outside of the body 510 of the device 500. In other embodiments, the actuator can be a dial, button, trigger, ratchet, and/or any other suitable mechanism. In other implementations, the flow separator 560 can be transitioned from the first state to the second state in response to a pressure differential (e.g., a negative pressure associated with the user inhaling or a positive pressure associated with a flow of fluid through the treatment passage 525.

Figure 31:
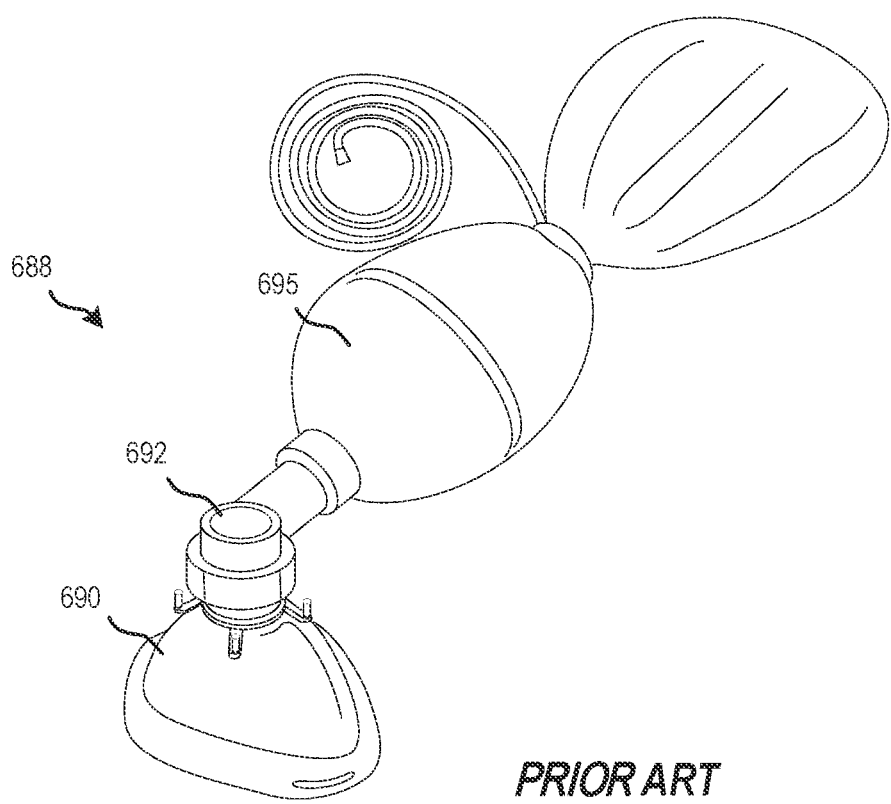
FIG. 31 is a perspective view of a known manual resuscitation device.
Figure 32:
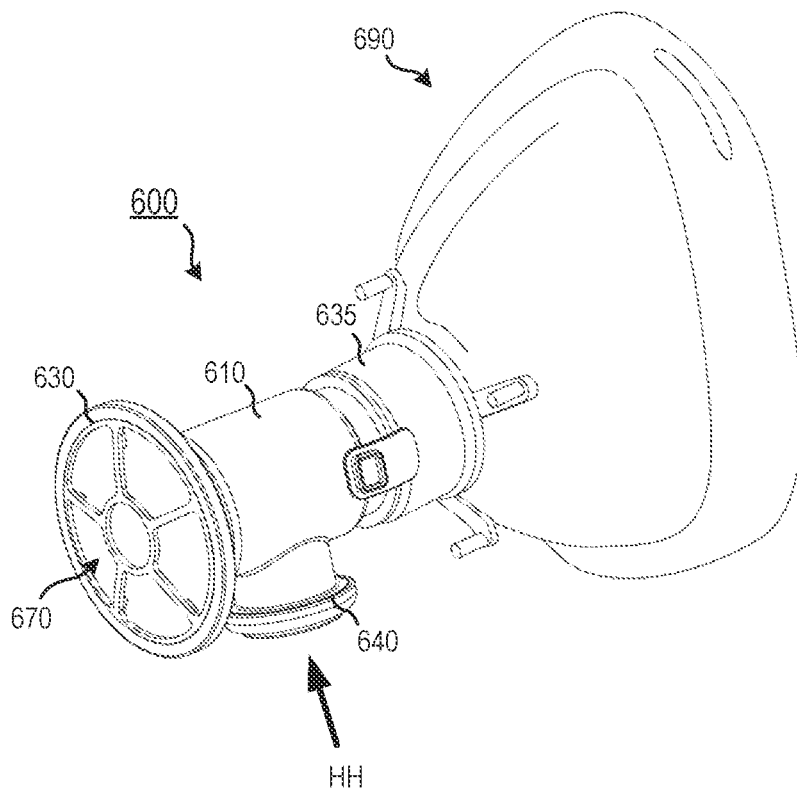
FIG. 32 is a perspective view of a respiratory isolation and treatment device according to an embodiment and shown coupled to, for example, a mask of a manual resuscitation device.

Any of the embodiments described herein can be used with any suitable treatment source or inlet gas source, and/or can be integrated into any suitable respiratory treatment/delivery system. By way of example, FIG. 31 shows a known manual resuscitation device 688 such as an AMBU® bag and/or the like. The manual resuscitation device 688 (referred to herein as "resuscitation device") includes a mask 690, a manifold 692 at least temporarily coupled to the mask 690, and a manual resuscitator 695 (e.g., a "bag") at least temporarily coupled to the manifold 692. In some implementations, any of the devices described herein can be used with the resuscitation device 688, for example, by replacing the manifold 692. For example, FIG. 32 shows a treatment device 600 having a body 610, a filter fitting 630, a mask fitting 635, and a treatment fitting 640. The device 600 can be similar to and/or substantially the same as the devices 100, 200, 300, 400, and/or 500 described in detail above. As such, the filter fitting 630 can include and/or can be at least temporarily coupled to a filter 670; the mask fitting 635 can be at least temporarily coupled to the mask 690 of the resuscitation device 688; and the treatment fitting 640 can be configured to receive and/or at least temporarily couple to the manual resuscitator 695 ("bag"), as indicated by the arrow HH in FIG. 32. In this manner, the device 600 can be integrated into the manual resuscitation device 688 and used to provide a flow of resuscitation air (from the manual resuscitator 695) to a user while concurrently filtering at least exhaled breath expelled by the user via the filter 670, as described in detail above with reference to previous embodiments.

Although not shown in FIG. 31, in some implementations, the device 600 can include a filter (e.g., a secondary filter that can be similar to the filter 670), that can be disposed in and/or along a fluid flow path between the manual resuscitator 695 and the treatment fitting 640 and/or treatment passage such that the resuscitation air provided to the user is also filtered. In some implementations, such a filter can be coupled to and/or included in the treatment fitting 640 (e.g., downstream or internal to a seal of the treatment fitting 640. In other implementations, the secondary filter can be included in an adapter or the like that is coupled between an output of the manual resuscitator 695 and the treatment fitting 640. While the manual resuscitator 695 is described as being at least temporarily coupled to the treatment fitting 640, in other implementations, the manual resuscitator 695 can be coupled, for example, to the filter fitting 630 to provide and/or allow for filtration of the resuscitation air provided to the user in addition to the filtration of the exhaled breath. In some implementations, the device 600 can be included in a kit or the like that includes an adapter, coupler, and/or fitting (with or without an integrated secondary filter) configured to allow the output of the manual resuscitator 695 to be coupled to at least one of the filter fitting 630 and/or the treatment fitting 640.

Figure 33:
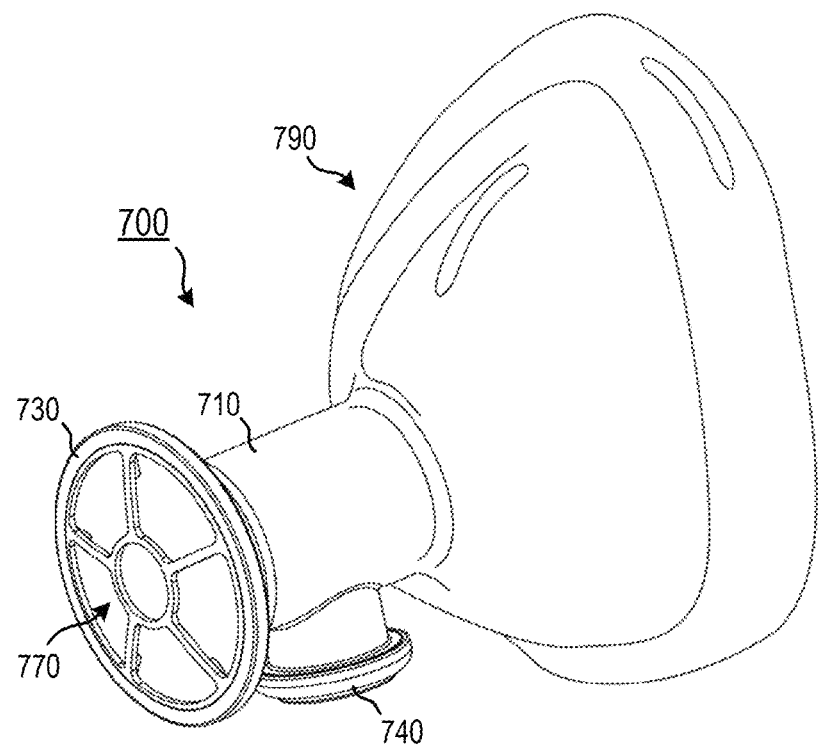
FIG. 33 is a perspective view of a respiratory isolation and treatment device having an integrated mask according to an embodiment.

While the devices 100, 200, 300, 400, 500, and/or 600 are described above as having a mask fitting that is at least temporarily coupled to a mask, hood, shield, and/or any other suitable user interface, in other embodiments, a treatment device can be integrally and/or unitarily formed with a mask and/or the like. For example, FIG. 33 illustrates a treatment device 700 according to an embodiment. The device 700 includes a body 710. A filter fitting 730 is disposed at a first end of the body 710 and can include and/or can be at least temporarily coupled to a filter 770, as described in detail above with reference to the devices 100, 200, 300, and/or 400. A treatment fitting 740 is disposed along the body 710 and is configured to at least temporarily couple to a treatment source such as, for example, an output of a compressed inlet gas source, a manual resuscitator, nebulizer, and/or any other suitable treatment device such as any of those described herein.

In this embodiment, a mask 790 is disposed at and/or integrated into a second end of the body 710. In some embodiments, the mask 790 can be similar to the mask 690 included in the manual resuscitation device 688 but adapted and/or modified such that a port or the like of the mask 790 is integrally formed during manufacturing with the second end of the body 710. Although not shown in FIG. 33, the mask 790 can include one or more straps, rings or loops (e.g., with a tightening mechanism, snaps, and/or ratchet), arm/hooks, and/or any other suitable attachment mechanism that can be placed around at least a portion of the user's head to temporarily couple the mask 790 to the user's head and/or face. As such, the device 700 can provide a respiratory treatment while filtering respiration air between a user donning the mask 790 and an environment outside of the device 700 via the filter 770, as described in detail above with reference to previous embodiments. While described above being integrated into and/or with the mask 790, it should be understood that the device 700 is presented by way of example only and not limitation. In other implementations, the body 710 of the device 700 can include and/or can be integrally formed with any suitable mask, hood, shield, etc., such as any of those described herein.

Figure 34:
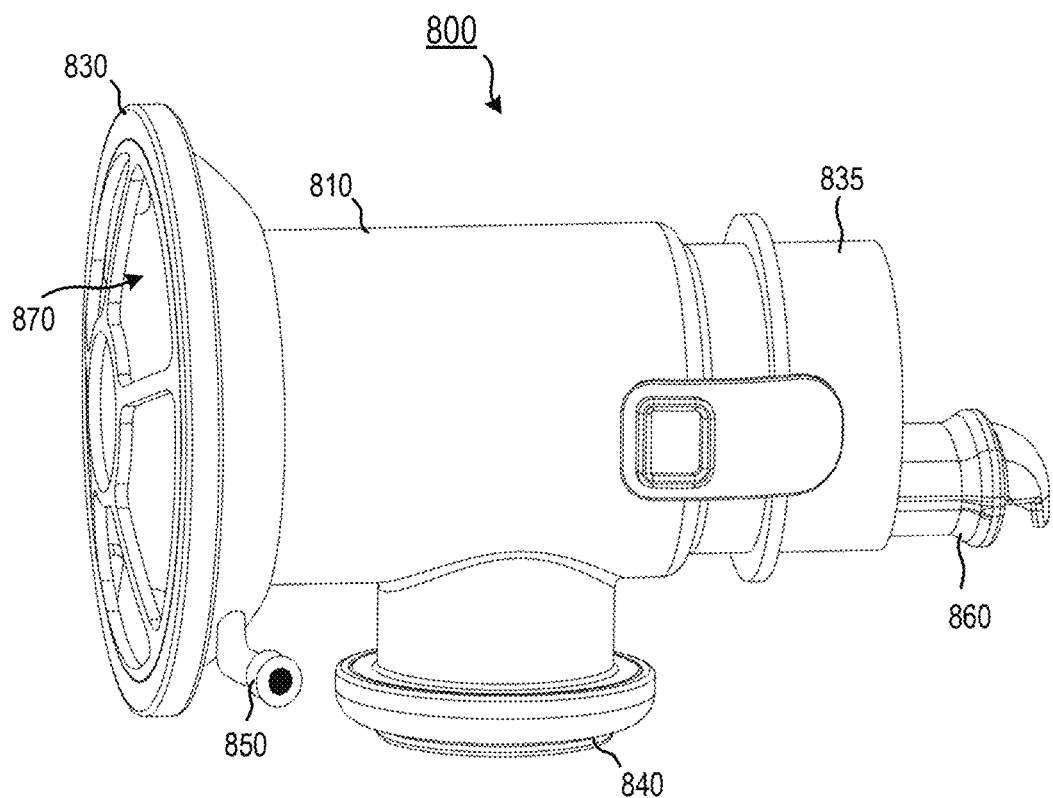
FIG. 34 is a side perspective view of a respiratory isolation and treatment device according to an embodiment and illustrating a condensation trap thereof.

FIG. 34 is a side perspective view of a treatment device 800 according to another embodiment. As shown, the device 800 includes a body 810, a filter fitting 830 disposed at a first end of the body 810, a mask fitting 835 disposed at and/or integrated into a second end of the body 810, a treatment fitting 840, and a flow separator 860. The filter fitting 830 can include and/or can be at least temporarily coupled to a filter 870. As such, the device 800 can be substantially similar in at least form and/or function to any of the devices 100, 200, 300, 400, 500, 600, and/or 700 described above. In this embodiment, however, the device 800 further includes a port 850 in fluid communication with at least one of a respiration passage and/or a treatment passage (not shown). For example, in some implementations, the port 850 can be in fluid communication with the respiration passage extending through the body 810 of the device 800 and can be configured to allow for the removal of condensation and/or any other fluid buildup within the respiration passage. Specifically, exhaled breath generally includes and/or carries aerosolized particles, moisture, bodily fluid, etc. which, in some instances, can at least partially condense within the respiration passage of the treatment 800. Accordingly, the port 850 can provide selective access into the respiration passage to allow the removal of condensation and/or any other fluid within the respiration device without removing the device 800 from the user and/or without otherwise allowing unfiltered exhaled breath to exit the device 800. The port 850 can be any suitable port such as a silicone seal, a self-healing port, a luer lock, a split septum, a needle free connector, and/or any other suitable port. In some implementation, the port 850 can be configured to receive and/or couple to, for example, a syringe and/or other suction device configured to draw the condensation and/or other fluid through the port 850.

While the port 850 is particular shown in FIG. 34 and described above as being in fluid communication with the respiration passage, it should be understood that a treatment device can include any number of ports in fluid communication with any suitable portion of the device. For example, a treatment device can include such a port in fluid communication with a treatment passage. In some embodiments, a treatment device can include a first port in fluid communication with the respiration passage and a second port in fluid communication with the treatment passage. In some embodiments, a treatment device can include such a port in or on a mask coupled to and/or integrated with a body of the device with or without including additional port(s) along the body. In some embodiments, a device and/or mask can provide and/or allow for the trapping of condensation with or without a port similar to the port 850. For example, such a device and/or mask can include an absorbent pad and/or material disposed within a portion of the body of the device and/or within a portion of the mask.

Figure 35:
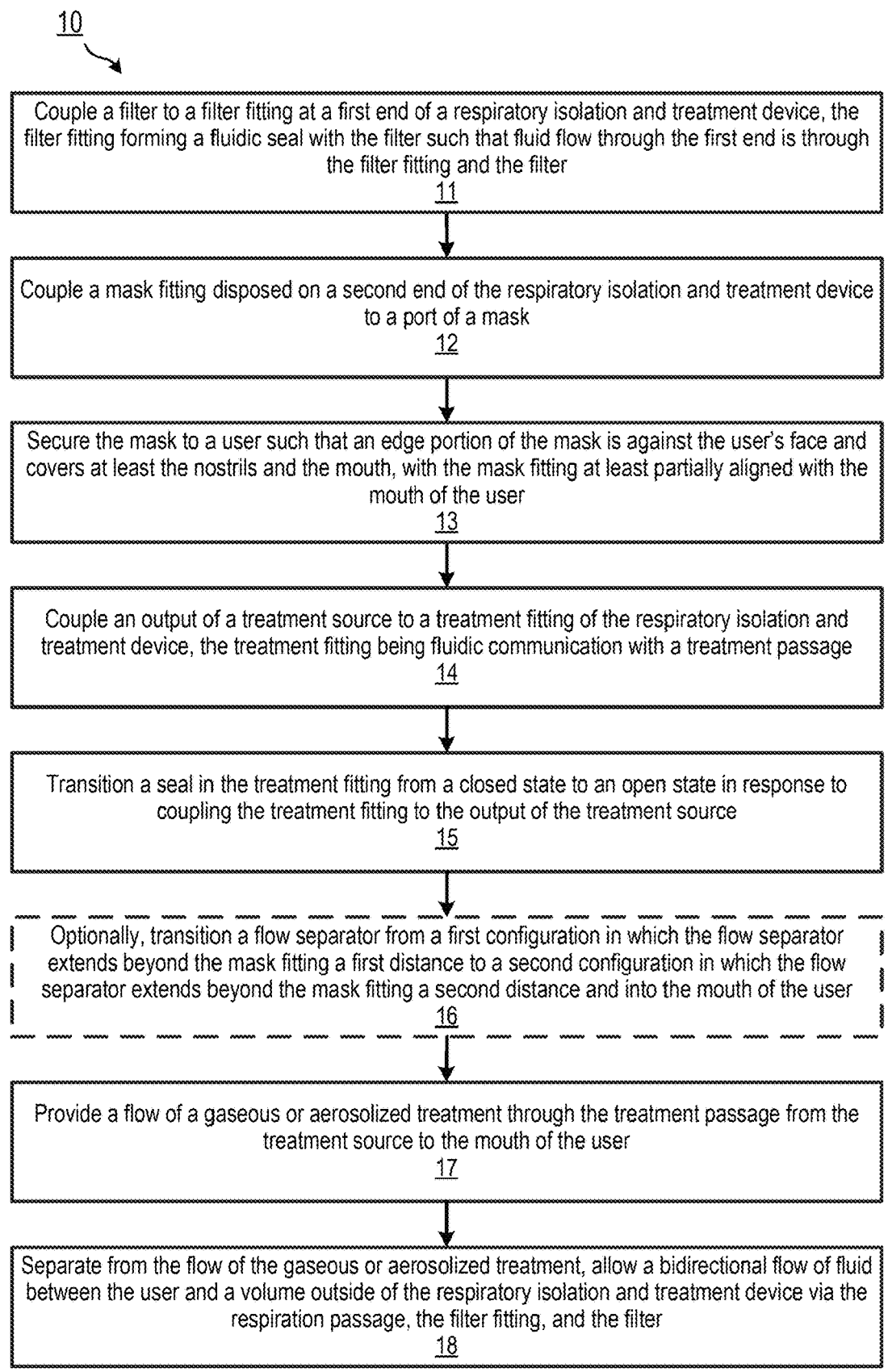
FIG. 35 is a flowchart illustrating a method of using a respiratory isolation and treatment device according to an implementation.

FIG. 35 is a flowchart illustrating a method 10 of using a respiratory isolation and treatment device according to an embodiment. The respiratory isolation and treatment device (also referred to herein as "device") can be similar to and/or substantially the same as any of the devices 100, 200, 300, 400, 500, 600, 700, and/or 800 described herein. For example, the device can include a body that defines a respiration passage extending through a first end and a second end of the body and a treatment passage extending through the second end of the body. A filter fitting can be disposed on the first end of the body and in fluidic communication with the respiration passage. A mask fitting can be disposed on the second end of the body and in fluidic communication with each of the respirator passage and the treatment passage. A treatment fitting can be disposed on or along the body and can be in fluidic communication with the treatment passage.

In some implementations, the method of using the device includes coupling a filter to the filter fitting disposed on the first end of the body, where the filter fitting and the filter collectively form a fluidic seal such that fluid flow through the first end of the body is through the filter fitting and the filter coupled thereto, at 11. For example, in some embodiments, the filter fitting and filter can be similar to the filter fitting 430 and the filter 470, respectively, described above. In this manner, the filter can include a seal, gasket, and/or the like that can form the fluidic seal around an opening of the filter fitting.

The mask fitting disposed on the second end of the body is coupled to a port of a mask, at 12. In some implementations, for example, the device can be used with a known mask, hood, shield, and/or the like and the mask fitting can be adapted to couple to an existing port of the known masks, etc. In some implementations, the mask fitting can include, for example, a locking mechanism, one or more latches, one or more couplers, and/or the like. In some implementations, the coupling of the mask fitting to the mask can be such that a substantially fluid-tight seal is formed between the mask fitting and a portion of the mask.

The mask is secured to a user such that an edge portion of the mask is placed against the face of the user and covers at least the nostrils and the mouth of the user, with the mask fitting at least partially aligned with the mouth of the user, at 13. For example, in some implementations, the mask can be a face mask configured to cover a portion of the user's face (e.g., at least the mouth and nostrils). In other implementations, the mask can be included in and/or a part of a hood that can be disposed about and/or that can otherwise substantially surround a user's head. When used with a hood, the mask or mask portion need not be placed against the face of the user.

An output of an inlet gas source, treatment source, and/or the like is coupled to the treatment fitting disposed on the body and in fluidic communication with the treatment passage, at 14. The treatment source can be any suitable device configured to deliver a gaseous or aerosolized treatment, therapeutic, medicament, and/or the like (e.g., a nebulizer or the like); an outlet of a reservoir, tank, canister, etc. containing a pressurized fluid such as air, oxygen ($O_2$), $O_2$ enriched air, nitric oxide (NO), nitrous oxide ($N_2O$) or other anesthetic gases, and/or any other suitable fluid (e.g., gas) or combination of fluids; a manual resuscitator such as an AMBU® bag or the like; and/or any other suitable device.

A seal disposed in the treatment fitting is transitioned from a closed state to an open state in response to coupling the output of the treatment source to the treatment fitting, at 15. For example, in some implementations, at least a portion of the output of the treatment source can be inserted into the treatment fitting and into contact with one or more portions of the seal. In some implementations, the seal can form a substantially fluid tight seal around a portion or surface of the output. In addition, the contact can with the seal can, for example, exert a force on a valve portion of the seal that is operable to transition the valve portion from a closed state to an open state. As described above with reference to the devices 200 and/or 300, the seal in the close state is configured to fluidically isolate the treatment passage from an opening defined by the treatment fitting and in the open state is configured to allow and/or establish fluid communication between the treatment source and the treatment passage through or via the treatment fitting.

As described above with reference to the device 500, in some embodiments, the device can include a flow separator that is configured to transition between two or more configuration. In some implementations, the method 10 may optionally include transitioning the flow separator from a first configuration in which the flow separator extends beyond the mask fitting a first distance to a second configuration in which the flow separator extends beyond the mask fitting a second distance and into the mouth of the user, at 16. In some embodiments, the device can include, for example, an external actuator or the like that a user can engage to transition the flow separator from the first configuration to the second configuration. In other embodiments, the user can clamp an end portion of the flow separator (e.g., with his or her teeth) and can pull the flow separator from the first configuration to the second configuration. In some implementations, the flow separator can be articulated, bent, flexed, bowed, rotated, and/or the like to allow an end portion of the flow separator to be disposed in the user's mouth. For example, at least a portion of the flow separator can be formed of a relatively soft and/or flexible material, can include a corrugation, living hinge, and/or any other configuration allowing for a desired amount of flexibility and/or reconfiguration.

A flow of a gaseous or aerosolized treatment is provided through the treatment passage from the treatment source to the mouth of the user, at 17. In some implementations, the treatment passage defines a unidirectional flow path configured to allow fluid to flow from the treatment source to the mouth of the user. Moreover, the flow of the gaseous or aerosolized treatment is separate and/or independent of a fluid flow through the respiration passage and/or other portion of the device. As described above, the therapeutic can be any suitable fluid. In some implementations, the treatment source can be a nebulizer or the like configured to nebulize a liquid therapeutic into an aerosolized fluid the particles of which can be carried by air. In some implementations, the therapeutic is provided in response to a suction force associated with the user inhaling. In other implementations, the therapeutic can be provided in response to a positive pressure within the treatment source (e.g., when the treatment source is a compressed gas such as air, oxygen, oxygen-enriched air, anesthetic and/or the like.

Separate from the flow of the gaseous or aerosolized treatment provided to the user, a bidirectional flow of fluid is allowed between the user and a volume outside of the device via the respiration passage, the filter fitting, and the filter coupled to the filter fitting, at 18. The bidirectional flow of fluid can be, for example, respiration air exchanged between the user and the environment outside of the device. With the bidirectional flow passing through the filter, the respiration air exchanged between the user and the environment outside of the device is filtered, thereby protecting the user and/or others in a surrounding environment from potentially infection and/or contagious aerosols that may be carried by the respiration air (e.g., in particular, the exhaled breath of the user). Moreover, the device provides and/or allows the bidirectional flow through the respiration passage and the unidirectional flow through the treatment passage in substantially concurrent and/or parallel process. Thus, the device can be used to provide respiratory treatment to users with potentially infectious and/or contagious illnesses such as, for example, the coronavirus leading the COVID-19 disease.

While various embodiments have been described herein, textually and/or graphically, it should be understood that they have been presented by way of example only, and not limitation. Likewise, it should be understood that the specific terminology used herein is for the purpose of describing particular embodiments and/or features or components thereof and is not intended to be limiting. Various modifications, changes, enhancements, and/or variations in form and/or detail may be made without departing from the scope of the disclosure and/or without altering the function and/or advantages thereof unless expressly stated otherwise. Functionally equivalent embodiments, implementations, and/or methods, in addition to those enumerated herein, will be apparent to those skilled in the art from the foregoing descriptions and are intended to fall within the scope of the disclosure.

For example, while the devices 100, 200, 300, 400, 500, 600, 700, and/or 800 are described herein as being used with particular device and/or in particular situations, it should be understood that they have been presented by way of example only and not limitation. The embodiments and/or devices described herein are not intended to be limited to any specific implementation unless expressly stated otherwise. For example, while the embodiments are described above as being used with, coupled to, and/or otherwise including a mask, hood, shield, etc., it should be understood that the embodiments and/or devices described herein can be used in any suitable respiratory treatment, therapy, ventilation, and/or breathing scenario. In some implementations, for example, any of the devices described herein can be added inline to any suitable respirator, ventilator, resuscitator, breather, oxygenator, and/or the like.

For example, in some implementations, the devices described herein can be used with, for example, a manual resuscitator such as, for example, an AMBU® bag and/or the like, as described above with reference to the device 600. While described above being coupled to a mask, hood, shield, and/or the like, in some implementations, any of the devices described herein can be coupled between, for example, an endotracheal tube, a nasotracheal tube, and/or the like (e.g., coupled to a mask or tube fitting) and a manual resuscitator, inlet fluid source, respirator, ventilator, and/or the like. In some implementations, any of the devices described herein can be coupled to a tracheostomy tube or the like (e.g., an indwelling tracheostomy tube connected to a mask or tracheostomy fitting) and can provide respiratory treatment, therapy, etc., as described in detail above. In some implementations, any of the devices and/or embodiments described herein can be used in any other suitable situation in which it is desirable to provide an inlet flow of a fluid (e.g., gas, air, $O_2$ enriched air, pure $O_2$, nebulized treatment or therapy, etc.).

Where schematics, embodiments, and/or implementations described above indicate certain components arranged and/or configured in certain orientations or positions, the arrangement of components may be modified, adjusted, optimized, etc. The specific size and/or specific shape of the various components can be different from the embodiments shown and/or can be otherwise modified, while still providing the functions as described herein. More specifically, the size and shape of the various components can be specifically selected for a desired or intended usage. Thus, it should be understood that the size, shape, and/or arrangement of the embodiments and/or components thereof can be adapted for a given use unless the context explicitly states otherwise. By way of example, in some implementations, a treatment device intended to provide treatment to an adult user may have a first size and/or shape, while a treatment device intended to provide treatment to a pediatric user may have a second size and/or shape smaller than the first size and/or shape. Moreover, the smaller size and/or shape of, for example, a pediatric treatment device may result in certain components being moved, reoriented, and/or rearranged while maintaining the desired function of the device.

Although various embodiments have been described as having particular characteristics, functions, components, elements, and/or features, other embodiments are possible having any combination and/or sub-combination of the characteristics, functions, components, elements, and/or features from any of the embodiments described herein, except mutually exclusive combinations or when clearly stated otherwise. For example, any of the devices 200, 300, 400, 500, 600, 700, and/or 800 described above can include and/or can be combined with a communication system similar to or substantially the same as the communication system described above with reference to the device 100. As another example, any of the devices described herein can include and/or can be combined with a bendable, movable, flexible, and/or otherwise reconfigurable flow separator as described above with reference to the device 500. Moreover, unless otherwise clearly indicated herein, any particular combination of components, functions, features, elements, etc. can be separated and/or segregated into independent components, functions, features, elements, etc. or can integrated into a single or unitary component, function, feature, element, etc.

Where methods described above indicate certain events occurring in certain order, the ordering of certain events may be modified. Additionally, certain of the events may be performed concurrently in a parallel process when possible, as well as performed sequentially as described above. While methods have been described as having particular steps and/or combinations of steps, other methods are possible having a combination of any steps from any of methods described herein, except mutually exclusive combinations and/or unless the context clearly states otherwise.

What is claimed:

1. A respiratory isolation and treatment device, the device comprising:
   a body defining a respiration passage extending through a first end and a second end of the body and a treatment passage extending through the second end of the body;
   a filter fitting disposed on the first end of the body and in fluidic communication with the respiration passage;
   a mask fitting disposed on the second end of the body and in fluidic communication with the respiration passage and the treatment passage;
   a treatment fitting disposed on the body and in selective fluidic communication with the treatment passage, the treatment fitting having a seal disposed therein and being transitionable from a closed state to an open state in response to the treatment fitting being coupled to an output of a treatment source, the seal in the closed state substantially preventing fluid flow through the treatment fitting and into or out of the treatment passage, the seal in the open state allowing fluidic communication between the treatment source and the treatment passage; and
   a flow separator at least partially disposed in the body, the flow separator defining a portion of the respiration passage and a portion of the treatment passage, the flow separator having a first end portion disposed in the body and terminating between the filter fitting and the treatment fitting, the flow separator having a second end portion extending through the mask fitting,
   the device configured to permit (i) inhalation air to be drawn into the filter fitting, through the respiration passage, and out of the mask fitting, (ii) exhaled breath to be expelled into the mask fitting, through the respiration passage, and out of the filter fitting, and (iii) a gaseous or aerosolized treatment to be drawn from the output of the treatment source when coupled to the treatment fitting, through the treatment passage, and out of the mask fitting, the first end portion of the flow separator including a valve selectively allowing a flow of exhaled breath out of the treatment passage and into the respiration passage.

2. The device of claim 1, wherein the respiration passage defines a bidirectional fluid flow path configured to allow a bidirectional flow of fluid between the filter fitting and the mask fitting.

3. The device of claim 1, wherein the treatment passage defines a unidirectional fluid flow path configured to allow a unidirectional flow of fluid from the treatment fitting to the mask fitting.

4. The device of claim 3, wherein the unidirectional fluid flow path defined by the treatment passage receives the unidirectional flow of the fluid, the fluid being the gaseous or aerosolized treatment from the treatment source and through the second end of the body when the treatment fitting is coupled to the treatment source and the seal is in the open state.

5. The device of claim 1, wherein the treatment source is an airflow delivery device configured to provide a gaseous flow of enriched air having a desired fraction of inspiration of oxygen (FiO2) through the output thereof.

6. The device of claim 1, wherein the treatment source is a nebulizer configured to provide the gaseous or aerosolized treatment.

7. The device of claim 1, wherein the filter fitting is configured to removably couple to a filter, the filter forming a fluidic seal with the filter fitting when coupled thereto.

8. The device of claim 7, wherein the filter is a high-efficiency particulate air (HEPA) filter.

9. The device of claim 7, wherein the filter fitting is configured to couple to the filter such that a flow of the inhalation air or the exhaled breath out of the first end of the body flows through the filter fitting and the filter coupled thereto.

10. The device of claim 7, wherein the filter is a first filter removably coupled to the filter fitting and being replaceable by a second filter, each of the first filter and the second filter including a back plate that forms a fluidic seal with the filter fitting such that a flow of the inhalation air or the exhaled breath through the first end of the body passes through at least one of the first filter or the second filter thereby entrapping contaminants within the flow.

11. The device of claim 1, wherein the valve of the flow separator has a closed state in which the respiration passage is fluidically isolated from the treatment passage within the body such that the gaseous or aerosolized treatment from the output of the treatment source flows through the treatment passage and not the respiration passage, the valve of the flow separator transitioning from the closed state to an open state in response to the flow of exhaled breath through the treatment passage.

12. The device of claim 1, wherein the valve disposed at the first end portion of the flow separator is aligned with the treatment fitting.

13. A respiratory isolation and treatment device, the device comprising:
- a body defining a respiration passage extending through a first end and a second end of the body and a treatment passage extending through the second end of the body;
- a filter fitting disposed on the first end of the body and in fluidic communication with the respiration passage, the filter fitting removably coupleable to a high-efficiency particulate air (HEPA) filter such that fluid flow through the first end of the body passes through the HEPA filter when coupled to the filter fitting;
- a mask fitting disposed on the second end of the body, a first portion of the mask fitting in fluidic communication with the respiration passage, a second portion of the mask fitting in fluidic communication with the treatment passage;
- a treatment fitting disposed on the body and in selective fluidic communication with the treatment passage, the treatment fitting having a seal disposed therein and being transitionable from a closed state to an open state in response to the treatment fitting being coupled to an output of a treatment source, the seal in the closed state substantially preventing fluid flow (i) through the treatment fitting and into the treatment passage and (ii) through the treatment passage and out of the treatment fitting, the seal in the open state allowing fluidic communication between the treatment source and the treatment passage; and
- a flow separator at least partially disposed in the body, the flow separator defining a portion of the respiration passage and a portion of the treatment passage, the flow separator having a first end portion adjacent to the treatment fitting and a second end portion extending through the mask fitting, the first end portion of the flow separator configured to permit a flow of a gaseous or aerosolized treatment from the output of the treatment source into the treatment passage and not the respiration passage, the first end portion of the flow separator having a valve configured to transition from a closed state to an open state to allow a flow of exhaled breath out of the treatment passage and into the respiration passage,
- the device configured to permit substantially contemporaneous bidirectional fluid flow through the respiration passage between the filter fitting and the first portion of the mask fitting and unidirectional fluid flow through the treatment fitting and the treatment passage and to the second portion of the mask fitting.

14. The device of claim 13, wherein the body defines a first axis extending through the respiration passage and a second axis extending through the treatment passage, the first axis and the second axis are substantially parallel and non-coaxial.

15. The device of claim 13, wherein the flow separator is configured to transition between first configuration in which the second end portion of the flow separator extends beyond the mask fitting a first distance and a second configuration in which the second end portion extends beyond the mask fitting a second distance greater than first distance, the second end portion of the flow separator configured to extend into the mouth of the user donning the mask when in the second configuration.

16. The device of claim 13, wherein the mask fitting is configured to be removably coupled to a port of a mask donned by a user, the respiration passage allowing a flow of inhalation air and the flow of exhaled breath between the user donning the mask and a volume outside of the body of the device via the HEPA filter, the treatment passage allowing the flow of the gaseous or aerosolized treatment from the treatment source coupled to the treatment fitting and into the mouth of the patient donning the mask.

17. The device of claim 13, wherein the respiration passage is fluidically isolated from the treatment passage within the body when the valve of the flow separator is in the closed state.

18. A kit, comprising:

a sealable packaging;

at least one filter removably disposed in the packaging; and a respiratory isolation and treatment device removably disposed in the packaging, the device including:

a body defining a respiration passage extending through a first end and a second end of the body and a treatment passage extending through the second end of the body, the body having a flow separator at least partially disposed therein and defining a portion of the respiration passage and a portion of the treatment passage, the flow separator having a first end portion disposed in the body and a second end portion extending through the mask fitting, the first end portion of the flow separator including a valve;

a filter fitting disposed on the first end of the body and in fluidic communication with the respiration passage, the at least one filter configured to removably couple to the filter fitting;

a mask fitting disposed on the second end of the body and in fluidic communication with the respiration passage and the treatment passage; and a treatment fitting disposed on the body in a position aligned with the valve included in the first end portion of the flow separator, the treatment fitting being in selective fluidic communication with the treatment passage, the treatment fitting having a seal disposed therein, the seal being in a closed state when the device is disposed in the packaging such that a flow of fluid through the treatment fitting is substantially prevented, the seal being transitionable to an open state when the device is outside of the packaging and the treatment fitting is coupled to an output of a treatment source to establish fluidic communication between the treatment source and the treatment passage.

19. The kit of claim 18, wherein the device is configured to permit substantially contemporaneous bidirectional fluid flow through the respiration passage between the filter fitting and a first portion of the mask fitting and unidirectional fluid flow through the treatment passage from the treatment fitting and to a second portion of the mask fitting.

20. The kit of claim 18, further comprising:
a mask having a port, the mask configured to be donned by a user such that (i) an outer edge of the mask is in contact with a face of the user and (ii) the mask covers at least the nostrils and the mouth of the user, the mask fitting of the device configured to removably couple to the port such that the mask fitting is aligned with the mouth of the user.

21. The kit of claim 18, wherein the at least one filter is at least one high-efficiency particulate air (HEPA) filter.

22. The kit of claim 18, wherein the at least one filter is configured to form a fluidic seal with the filter fitting of the device when coupled thereto.

23. The kit of claim 18, wherein the at least one filter includes a first filter and a second filter, the first filter configured to be coupled to the filter fitting of the device such that a fluid flow through the first end of the body of the device is through the filter fitting and the filter coupled thereto, and
the filter fitting being configured to allow the first filter removably coupled to the filter fitting to be replaced with the second filter while substantially limiting the fluid flow through the first end of the body to a flow through at least one of the first filter or the second filter.

24. The kit of claim 18, wherein the valve of the flow separator of the device has a closed state in which the respiration passage is fluidically isolated from the treatment passage within the body such that the gaseous or aerosolized treatment from the output of the treatment source flows through the treatment passage and not the respiration passage, the valve of the flow separator configured to transition from the closed state to an open state in response to a flow of exhaled breath through the treatment passage, the valve of the flow separator in the open state allowing the exhaled breath to flow out of the treatment passage and into the respiration passage.

25. A method of using a respiratory isolation and treatment device to deliver a gaseous or aerosolized treatment, the device including a body that defines a respiration passage extending through a first end and a second end of the body and a treatment passage extending through the second end of the body, the body including a flow separator defining a portion of the respiration passage and a portion of the treatment passage, the method comprising:
coupling a filter to a filter fitting disposed on the first end of the body and in fluidic communication with the respiration passage, the filter fitting and the filter collectively forming a fluidic seal such that fluid flow through the first end of the body is through the filter fitting and the filter coupled thereto;
coupling a mask fitting disposed on the second end of the body to a port of a mask;
securing the mask to a user such that (i) an edge portion of the mask is placed against the face of the user, (ii) the mask covers at least the nostrils and the mouth of the user, and (iii) the mask fitting is aligned with the mouth of the user;
coupling an output of a treatment source to a treatment fitting disposed on the body and in fluidic communication with the treatment passage;
transitioning a seal disposed in the treatment fitting from a closed state to an open state in response to the coupling the treatment fitting to the output of the treatment source;
providing a flow of a gaseous or aerosolized treatment through the treatment passage from the treatment source to the mouth of the user, a valve of the flow separator being in a closed state during the providing, the valve being disposed at an end portion of the flow separator and aligned with the treatment fitting;
transitioning the valve disposed at the first end portion of the flow separator from the closed state to an open state in response to a flow of exhaled breath through the treatment passage; and
allowing a bidirectional flow of fluid between the user and a volume outside of the device via the respiration passage, the filter fitting, and the filter coupled thereto, the bidirectional flow of fluid being separate from the flow of the gaseous or aerosolized treatment provided to the user.

26. The method of claim 25, wherein the providing the flow of the gaseous or aerosolized treatment via the treatment passage is substantially contemporaneous with the allowing the bidirectional flow fluid via the respiration passage.

27. The method of claim 25, wherein a first axis extends through the respiration passage and a second axis extends through the treatment passage, the first axis and the second axis are substantially parallel and non-coaxial.

28. The method of claim 25, wherein
the end portion of the flow separator is a first end portion of the flow separator adjacent to the treatment fitting, the first end portion of the flow separator configured to permit the flow of the gaseous or aerosolized treatment from the output of the treatment source into the treatment passage and not the respiration passage when the valve is in the closed state, and
the flow separator having a second end portion opposite the first end portion, the second end portion extending beyond the mask fitting and into a volume defined by the mask when the mask fitting is coupled to the mask.

29. The method of claim 28, further comprising:
transitioning the flow separator from a first configuration in which the second end portion of the flow separator extends beyond the mask fitting a first distance to a second configuration in which the second end portion of the flow separator extends beyond the mask fitting a second distance, greater than first distance, such that the second end portion extends into the mouth of the user donning the mask.

30. The method of claim 25, wherein the device includes a condensation port, the method further comprising:
aspirating, via the condensation port, condensation accumulated within at least one of the device or the mask.

* * * * *